(12) United States Patent
Cully et al.

(10) Patent No.: US 10,926,064 B2
(45) Date of Patent: *Feb. 23, 2021

(54) VASCULAR OCCLUSION AND DRUG DELIVERY DEVICES, SYSTEMS, AND METHODS

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); Douglas S. Paget, Flagstaff, AZ (US); Rachel Radspinner, Flagstaff, AZ (US); Edward E. Shaw, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 127 days.

This patent is subject to a terminal disclaimer.

(21) Appl. No.: 15/882,163

(22) Filed: Jan. 29, 2018

(65) Prior Publication Data

US 2018/0154120 A1   Jun. 7, 2018

Related U.S. Application Data

(63) Continuation of application No. 13/914,473, filed on Jun. 10, 2013, now Pat. No. 9,878,132.
(Continued)

(51) Int. Cl.
*A61M 25/10* (2013.01)
*A61B 17/12* (2006.01)
(Continued)

(52) U.S. Cl.
CPC ....... *A61M 25/10* (2013.01); *A61B 17/12022* (2013.01); *A61B 17/12109* (2013.01);
(Continued)

(58) Field of Classification Search
CPC ............ A61M 5/00; A61M 2025/1004; A61M 2025/105; A61M 2025/1065;
(Continued)

(56) References Cited

U.S. PATENT DOCUMENTS

| 5,074,845 A | 12/1991 | Miraki et al. |
| 5,232,444 A | 8/1993 | Just et al. |

(Continued)

FOREIGN PATENT DOCUMENTS

| CN | 201200438 Y | 3/2009 |
| CN | 101978934 A | 2/2011 |

(Continued)

OTHER PUBLICATIONS

International Search Report for PCT/US2013/045483 dated Oct. 24, 2013, corresponding to U.S. Appl. No. 13/914,464.
(Continued)

*Primary Examiner* — Theodore J Stigell

(57) ABSTRACT

Embodiments of the present disclosure comprise occlusion and drug delivery devices and methods. One aspect of the disclosure comprises a drug delivery device comprising an inner expansion member and an outer drug delivery component. Another aspect of the disclosure comprises bioabsorbable, lumen-occluding implants.

12 Claims, 16 Drawing Sheets

Related U.S. Application Data

(60) Provisional application No. 61/660,615, filed on Jun. 15, 2012.

(51) Int. Cl.
*A61M 5/00* (2006.01)
*A61B 17/00* (2006.01)

(52) U.S. Cl.
CPC .......... *A61B 17/12131* (2013.01); *A61M 5/00* (2013.01); *A61B 17/1214* (2013.01); *A61B 17/12145* (2013.01); *A61B 17/12159* (2013.01); *A61B 17/12181* (2013.01); *A61B 2017/00004* (2013.01); *A61B 2017/00778* (2013.01); *A61B 2017/00884* (2013.01); *A61B 2017/00893* (2013.01); *A61M 2025/1004* (2013.01); *A61M 2025/105* (2013.01); *A61M 2025/1065* (2013.01)

(58) Field of Classification Search
CPC ............. A61M 25/10; A61B 17/12131; A61B 17/12109; A61B 17/12022; A61B 17/1214; A61B 17/12145; A61B 17/12159; A61B 17/12181
USPC .......................... 604/101.02, 103.01, 103.02
See application file for complete search history.

(56) References Cited

U.S. PATENT DOCUMENTS

| | | | |
|---|---|---|---|
| 5,282,785 A | 2/1994 | Shapland et al. | |
| 5,336,178 A * | 8/1994 | Kaplan | A61B 8/12 604/103.01 |
| 5,431,173 A * | 7/1995 | Chin | A61B 17/00234 128/898 |
| 5,499,971 A | 3/1996 | Shapland et al. | |
| 5,989,280 A | 11/1999 | Euteneuer et al. | |
| 6,200,257 B1 | 3/2001 | Winkler | |
| 6,398,758 B1 | 6/2002 | Jacobsen et al. | |
| 6,960,222 B2 | 11/2005 | Vo et al. | |
| 7,524,275 B2 | 4/2009 | Patrick et al. | |
| 7,637,886 B2 * | 12/2009 | Herweck | A61L 29/041 604/103.01 |
| 9,381,326 B2 | 7/2016 | Cully et al. | |
| 9,878,132 B2 | 1/2018 | Cully et al. | |
| 2001/0035456 A1 | 11/2001 | Lennox | |
| 2002/0091398 A1 | 7/2002 | Galdonik et al. | |
| 2002/0147445 A1 | 10/2002 | Farley et al. | |
| 2003/0040705 A1 | 2/2003 | Dorros et al. | |
| 2003/0105508 A1 | 6/2003 | Johnson et al. | |
| 2004/0087902 A1 | 5/2004 | Richter | |
| 2005/0015047 A1 | 1/2005 | Shah | |
| 2005/0021080 A1 | 1/2005 | Feuer et al. | |
| 2005/0107653 A1 | 5/2005 | Patrick et al. | |
| 2005/0133046 A1 | 6/2005 | Becker et al. | |
| 2005/0216054 A1 | 9/2005 | Widomski et al. | |
| 2006/0030923 A1 | 2/2006 | Gunderson | |
| 2007/0073271 A1 | 3/2007 | Brucker et al. | |
| 2007/0173785 A1 | 7/2007 | Ostroot | |
| 2007/0243228 A1 | 10/2007 | McKay | |
| 2008/0004657 A1 | 1/2008 | Obermiller et al. | |
| 2008/0015500 A1 | 1/2008 | Herweck et al. | |
| 2008/0228257 A1 | 9/2008 | Richter | |
| 2008/0243068 A1 | 10/2008 | Ramzipoor et al. | |
| 2008/0255509 A1 | 10/2008 | Wang | |
| 2009/0018637 A1 | 1/2009 | Paul et al. | |
| 2009/0105687 A1 | 4/2009 | Deckman et al. | |
| 2009/0148492 A1 | 6/2009 | Dave | |
| 2009/0299374 A1 | 12/2009 | Tilson et al. | |
| 2010/0016874 A1 | 1/2010 | Lieberman | |
| 2010/0125239 A1 | 5/2010 | Perry et al. | |
| 2010/0256600 A1 | 10/2010 | Ferrera | |
| 2011/0040365 A1 | 2/2011 | Hirszowicz et al. | |
| 2011/0046724 A1 | 2/2011 | Heilmann et al. | |
| 2011/0130708 A1 | 6/2011 | Perry et al. | |
| 2012/0018090 A1 | 1/2012 | Horn et al. | |
| 2012/0041393 A1 | 2/2012 | Ahmann et al. | |
| 2012/0310210 A1 | 12/2012 | Campbell et al. | |
| 2012/0323271 A1 | 12/2012 | Obermiller et al. | |
| 2013/0204345 A1 | 8/2013 | Cully et al. | |
| 2013/0226131 A1 | 8/2013 | Bacino et al. | |
| 2013/0253426 A1 | 9/2013 | Campbell | |

FOREIGN PATENT DOCUMENTS

| | | |
|---|---|---|
| EP | 2586386 A2 | 5/2013 |
| JP | 2002-513609 | 5/2002 |
| JP | 2007-500545 A | 1/2007 |
| WO | WO-80/00720 | 4/1980 |
| WO | WO-95/20416 | 8/1995 |
| WO | WO-99/27989 A1 | 6/1999 |
| WO | WO-01/13800 A1 | 3/2001 |
| WO | WO-03/043539 | 5/2003 |
| WO | WO-2005/049141 | 6/2005 |
| WO | WO-2006/081238 | 8/2006 |
| WO | 2009/009275 A1 | 1/2009 |
| WO | WO-2009/009466 A1 | 1/2009 |
| WO | WO-2009/096822 A1 | 8/2009 |
| WO | WO-2009111716 A1 | 9/2009 |
| WO | WO-2010016923 A1 | 2/2010 |
| WO | WO-2010/028300 A1 | 3/2010 |
| WO | WO-2012/170538 A2 | 12/2012 |
| WO | WO-2013/066566 A1 | 5/2013 |

OTHER PUBLICATIONS

International Search Report for PCT/US2013/045490 dated Oct. 25, 2013.
International Preliminary Report on Patentability received for PCT Patent Application No. PCT/US2013/045483, dated Dec. 24, 2014, 12 pages.
International Preliminary Report on Patentability received for PCT Patent Application No. PCT/US2013/045490, dated Dec. 24, 2014, 8 pages.
International Written Opinion received for PCT Patent Application No. PCT/US2013/045483, dated Oct. 24, 2013, 10 pages.
International Written Opinion received for PCT Patent Application No. PCT/US2013/045490, dated Oct. 25, 2013, 6 pages.

* cited by examiner

VASCULAR OCCLUSION AND DRUG DELIVERY DEVICES, SYSTEMS, AND METHODS

CROSS REFERENCE TO RELATED APPLICATIONS

This patent application claims priority to and the benefit of Provisional Patent Application Ser. No. 61/660,615, entitled VASCULAR OCCLUSION AND DRUG DELIVERY DEVICES, SYSTEMS, AND METHODS, filed Jun. 15, 2012, which is incorporated by reference herein in its entirety.

BACKGROUND

Field

The present disclosure relates to occlusion and drug delivery devices, systems, and methods. Such devices and methods can be useful for tissue ablation, tissue and/or vascular drug delivery, and temporary and/or permanent vessel occlusion.

Discussion of the Related Art

The systemic administration of therapeutic agents treats the body as a whole even though the disease to be treated may be localized. In some cases of localized condition or disease, systemic administration may not be desirable because the drug agents may have deleterious or unwanted effects on parts of the body which are not to be treated or because treatment of the diseased part of the body requires a high concentration of drug agent that may not be achievable by systemic administration. It is therefore often desirable to administer therapeutic agents to only localized sites within the body. Common examples of where this is needed include cases of localized disease (e.g., heart disease and saphenous vein incompetence) and occlusions or lesions in body lumens. Several devices and methods for localized drug delivery are known.

Typically, with these types of treatments, an elongate member, such as a catheter, traverses the vasculature with a drug containing device mounted on the end. Once the target area is reached, the drug containing device delivers the drug. While the specifics of the drug containing device and the mode of delivery can vary, the problems encountered with these devices are usually the same.

Some of the problems encountered include dilution of the therapeutic agent with body fluids, migration away from the treatment area, and adverse effects caused by the migration. For example, in a method of treating an incompetent saphenous vein, chemical ablation involves treating the target vessel with a sclerosant that actually injures the contacted tissue. As expected by its effect, sclerosants are highly toxic and thus migration should be avoided to the extent possible to minimize unwanted side effects. Sclerosant migration through the vasculature has been linked with deep venous thrombosis, pulmonary embolism, ulceration and neurological events such as migraines, transient ischemic attacks and cerebrovascular accidents. In addition, sclerosants can have a high price per unit, so minimizing the amount utilized to effect treatment is also desirable.

Complicating the ability of designing drug delivery devices and modes of treatment that minimize the issues discussed above is the tortuosity of the vessel, both traversing a tortuous, narrow vessel and treating a tortuous section of a vessel. For example, tortuosity often occurs in the Greater Saphenous Vein (GSV) and can pose difficulty. In the case of the GSV, the treatment site may be, for example, 30-40 cm or more of a tortuous vein.

As can be appreciated by the example of saphenous vein sclerotherapy, improvements in vascular drug delivery that improve delivery rates or efficacy, minimize dilution, and/or minimize migration are desired.

SUMMARY

The present disclosure is directed to devices and methods for use in connection with drug delivery and/or vessel occlusion, useful in the treatment of numerous conditions, such as saphenous vein incompetency. Disclosed devices can be operable for providing close proximity to a surrounding tissue defining a lumen along a length of the device and further, applying a therapeutic agent, to the surrounding tissue along this length. Stated differently, the therapeutic agent can be intimately applied to at least a majority portion of the surrounding tissue along this length.

Additionally, disclosed devices can displace at least a portion of a fluid, such as blood, along the length of a vessel and thus, substantially occlude the vessel along this length. In effect, the close proximity to the surrounding tissue and the displacement of blood can reduce the amount of therapeutic agent required for an effective treatment as well as the amount of therapeutic agent migrating away from the treatment site.

In accordance with an aspect of the present disclosure, drug delivery and/or occlusion devices and methods comprise an expandable member and a drug delivery component that facilitate the application of a therapeutic agent to a surrounding tissue defining a lumen along a length. In some embodiments, a device is operable to evert and thereby extend along the length of the vessel to be treated. Once in position, a device can be operable to deliver a therapeutic agent to the surrounding tissue, upon pressurization of the expandable member at pressures less than 20 psi. The drug delivery component can be infused with a therapeutic agent, while located in the vasculature prior to pressurization, or in some embodiments, the drug delivery component can be infused or imbibed with a therapeutic agent prior to the introduction of the device into the vasculature. Once therapeutic agent has been transferred to the surrounding tissue, the expandable member is collapsed and then the expandable member and the drug delivery component are retracted.

In accordance with another aspect of the disclosure, drug delivery and/or occlusion devices and methods can comprise a bioabsorbable, lumen-occluding implant (bioabsorbable implant) member. Bioabsorbable implants can have an occlusive or flow stasis effect and also contribute to augment healing. Embodiments can be implanted via an implantation guide, such as a hollow needle or catheter, into the lumen of a vessel or into a tissue or body cavity. In some embodiments, the bioabsorbable, implant can be extended and retracted on demand to adjust the position of the bioabsorbable implant. In some embodiments, the bioabsorbable implant can be anchorable. In some embodiments, the bioabsorbable implant can have a narrow delivery profile and a wider implantation profile.

Bioabsorbable implant embodiments can further be imbibed with a therapeutic agent. The same or different embodiments can be configured to cause a thrombogenic response and/or a spasmodic response to have an occlusive effect. In some embodiments, imbibing can be performed on demand, e.g., with the use of a pressurizable capsule. The pressurizable capsule or other imbibing mode can be integrated into the delivery device.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein:

FIG. 3C-1 to FIG. 3C-5 illustrate the steps of implanting an occluding device embodiment into a vessel;

FIG. 4A-1 illustrates an occluding device embodiment;

FIG. 4A-2 illustrates an occluding device embodiment during release from a implantation guide;

FIG. 4B-1 illustrates a proximal end of an occluding device embodiment inserted into a distal end of an implantation piston member embodiment;

FIG. 4B-2 illustrates the control end of a delivery device embodiment;

FIGS. 4C-1 and 4C-2 illustrate a distal end of a delivery device embodiment comprising a cutter mechanism;

FIG. 5A-1 illustrates a first component of a bioabsorbable implant embodiment delivered to a treatment site via a guidewire;

FIGS. 5A-2 and 5A-3 illustrates a implantation guide inserted into the first component of the bioabsorbable implant; and FIGS. 5A-4 and 5A-5 illustrate an implantation guide injecting the second component of bioabsorbable implant into the first component of the bioabsorbable implant.

DETAILED DESCRIPTION

Figure 1A:
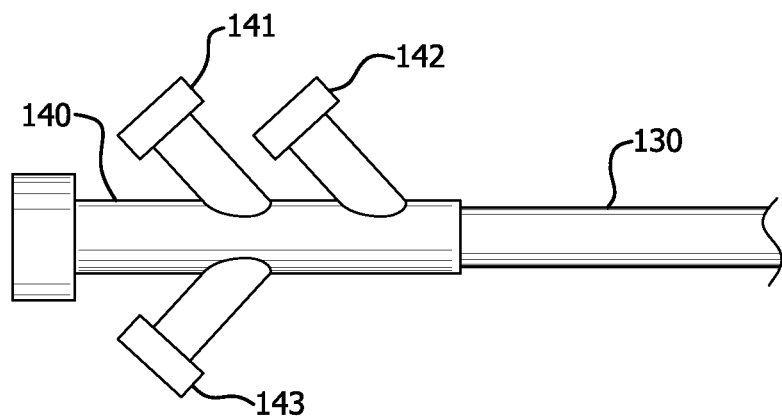
FIG. 1A illustrates a top view of a hub comprising an expansion port, an infusion port, and a ventilation port.

Persons skilled in the art will readily appreciate that various aspects of the present disclosure can be realized by any number of methods and apparatuses capable of performing the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

Although the present disclosure can be described in connection with various principles and beliefs, the present disclosure should not be bound by theory. For example, the present disclosure can be described herein in connection with occlusion and drug delivery in the context of the vasculature. However, the present disclosure can be applied toward any space-filling and/or chemical agent delivery devices or methods of similar structure and/or function. Furthermore, the present disclosure can be applied in non-vascular applications and even non-biologic and/or non-medical applications.

The terms "proximal" and "distal," when used herein in relation to a device or device component refer to directions closer to and farther away from the operator of the device, respectively. Since the present disclosure is not limited to peripheral or central approaches, the device should not be narrowly construed when using the terms proximal or distal since device features can be slightly altered relative to the anatomical features and the device position relative thereto.

The term "lumen" or "body lumen", as used herein in the context of the treatment site, comprises any vessel lumen or body cavity. "Vessel," as used herein, can include an artery or vein or any other body conduit such as a gastro-intestinal tract, fallopian tube, or the like.

The term "infuse" as used herein, refers to spreading over, through, or in between something, and includes to permeate, fill, suffuse, infuse, or the like. Similarly, the term "infusible" as used herein, refers to the ability to be infused. Embodiments described herein can be infused with a therapeutic agent for purposes of applying the therapeutic agent to a surrounding area or tissue.

The term "imbibe" as used herein, refers to absorbing, saturating, bonding, and/or coating something. Embodiments described herein can be imbibed with a therapeutic agent for purposes of applying the therapeutic agent to a surrounding tissue.

The term "permeability" as used herein, refers to the ability to transmit fluids (liquid or gas) through the pores of a membrane or filter material when the material is subjected to a differential pressure across it. Permeability can be characterized by Gurley number, Frazier number, or water flux rate. Embodiments described herein can be configured to transmit a fluid at low differential pressures.

The term "bioabsorbable" or "absorption" refers to the physiological process in which at least a portion of a material hydrolyzes, degrades, dissolves, absorbs, resorbs, or otherwise assimilates into the body.

The term "therapeutic agent" or "drug" as used herein, refers to any substance that aids in any procedure, e.g., diagnostic or therapeutic procedures, or that aids in providing a therapeutic and/or curative effect.

Such agents include, but are not limited to, sclerosants, such as polidocanol (Aethoxysklerol), sodium teradecylsulfate (STS, Sotradecol), ethanolamine oleate (ethamolin), Sodium morrhuate (Scleromate), concentrated ethanol (>90%), concentrated phenol (~3%), hypertonic saline, hypertonic dextrose solutions (e.g. Sclerodex® produced by Omega Laboratories), chromated glycerin (Sklermo® or Chromex®), and glycerin-based sclerosants; anti-thrombotic agents such as heparin, heparin derivatives (low molecular weight heparins, danaparoid, and fondaparinux), thrombolytics (urokinase, etc.), and dextrophenylalanine proline arginine, chloromethylketone, Coumadin, Coumarin, and direct thrombin inhibitors such as argatroban; anti-inflammatory agents such as dexamethasone, prednisolone, corticosterone, budesonide, estrogen, sulfasalazine and mesalamine, sirolimus and everolimus (and related analogs), anti-neoplastic/antiproliferative/antimiotic agents such as paclitaxel and analogues thereof, paclitaxel protein-bound particles such as ABRAXANE® (ABRAXANE is a registered trademark of ABRAXIS BIOSCIENCE, LLC), paclitaxel complexed with an appropriate cyclodexdrin (or cyclodextrin like molecule), rapamycin and analogues thereof, rapamycin (or rapamycin analogs) complexed with an appropriate cyclodexdrin (or cyclodextrin like molecule), beta-lapachone and analogues thereof, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide containing compound, AZX1 00 a cell peptide that mimics HSP20 (Capstone Therapeutics Corp., USA), heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation effectors; vasodilating agents; agents that interfere with endogenous vasoactive mechanisms; inhibitors of leukocyte recruitment, such as monoclonal antibodies; cytokines; hormones or a combination thereof. In an embodiment, therapeutic agent can comprise a biocompatible glue or tissue adhesive. Similarly, a therapeutic agent can comprise procoagulants, such as fibrin glue and/or thrombin administration. In one embodiment, said therapeutic agent is a hydrophilic agent. In another embodiment, said therapeutic agent is a hydrophobic agent. In another embodiment, said therapeutic agent is paclitaxel.

The therapeutic agents useful in conjunction with the present disclosure can be delivered to the tissue in various physical forms, including but not limited to nanospheres, microspheres, nanoparticles, microparticles, crystallites, inclusion complexes, emulsions, gels, foams, creams, suspensions, and solutions or any combination thereof. In one embodiment, the agent is delivered to the tissue in a solubilized form. In another embodiment, the agent is delivered to the tissue in a gel.

The present disclosure is directed to devices and methods for use in connection with drug delivery and/or vessel occlusion, useful in the treatment of numerous conditions, such as saphenous vein incompetency. Disclosed devices can be operable for providing close proximity to a surrounding tissue defining a lumen along a length of the device and applying a therapeutic agent, to the surrounding tissue along this length. For example, the therapeutic agent can be intimately applied to at least a majority portion of the surrounding tissue along this length.

Additionally, disclosed devices can displace at least a portion of a fluid, such as blood, along the length of a vessel and thus, substantially occlude the vessel along this length. In effect, the close proximity to the surrounding tissue and the displacement of blood can reduce the amount of therapeutic agent required for an effective treatment as well as the amount of therapeutic agent migrating away from the treatment site.

In accordance with an aspect of the present disclosure, drug delivery and/or occlusion devices and methods comprise an expandable member and a drug delivery component that facilitate the application of a therapeutic agent to a surrounding tissue defining a lumen along a length. In some embodiments, a device is operable to evert and thereby extend along the length of the vessel to be treated. Once in position, a device can be operable to deliver a therapeutic agent to the surrounding tissue, upon pressurization of the expandable member at pressures less than 20 psi. The drug delivery component can be infused with a therapeutic agent, while located in the vasculature prior to pressurization, or in some embodiments, the drug delivery component can be infused or imbibed with a therapeutic agent prior to the introduction of the device into the vasculature. Once therapeutic agent has been transferred to the surrounding tissue, the expandable member is collapsed and then the expandable member and the drug delivery component are retracted.

In accordance with another aspect of the disclosure, drug delivery and/or occlusion devices and methods can comprise a bioabsorbable, lumen-occluding implant (bioabsorbable implant) member. Bioabsorbable implants can have an occlusive or flow stasis effect and also contribute to augment healing. Embodiments can be implanted via an implantation guide, such as a hollow needle or catheter, into the lumen of a vessel or into a tissue or body cavity. In some embodiments, the bioabsorbable, implant can be extended and retracted on demand to adjust the position of the bioabsorbable implant. In some embodiments, the bioabsorbable implant can be anchorable. In some embodiments, the bioabsorbable implant can have a narrow delivery profile and a wider implantation profile.

Bioabsorbable implant embodiments can further be imbibed with a therapeutic agent. The same or different embodiments can be configured to cause a thrombogenic response and/or a spasmodic response to have an occlusive effect. In some embodiments, imbibing can be performed on demand, e.g., with the use of a pressurizable capsule. The pressurizable capsule or other imbibing mode can be integrated into the delivery device.

Figure 1B:
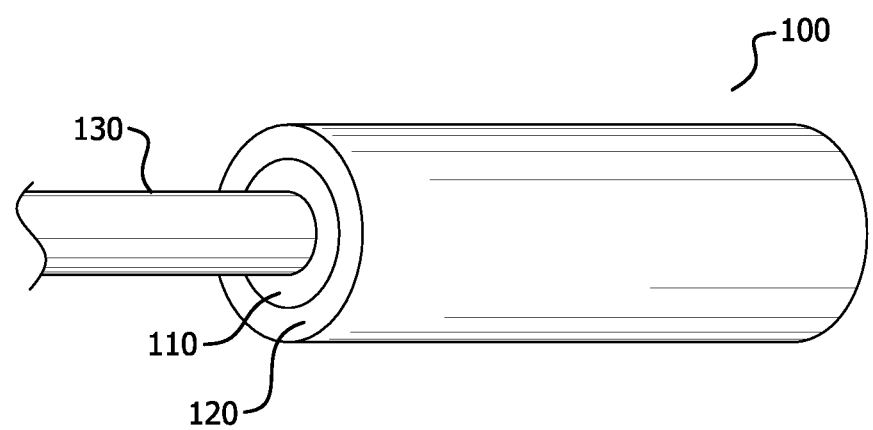
FIG. 1B illustrates a perspective, schematic view of a vascular drug delivery device.

With reference to FIGS. 1A and 1B, in accordance with various embodiments, a vascular drug delivery device 100 can comprise an inner expandable member 110 and an outer drug delivery component 120, inner and outer being in reference to the relative location when device 100 is in an extended configuration. In such configuration, drug delivery component 120 can circumscribe or be mounted around at least a portion of the length of the expandable member 110.

Drug delivery component 120 is any structural component suitable for transferring a therapeutic agent from component to a surrounding tissue that defines a lumen. Drug delivery component 120 is configured to be in close proximity to the surrounding tissue along a length of device 100 and permit application of a therapeutic agent to the surrounding tissue along this length. In an embodiment, drug delivery component 120 can intimately transfer a therapeutic agent to at least a majority portion of the surrounding tissue along this length. In some embodiments, drug delivery component 120 can be imbibed or infused with a therapeutic agent.

Expandable member 110 is any structural component or material suitable for expanding into close proximity to the surrounding tissue along a length of the device. For example, expandable member 110 can be an inflatable device, such as a balloon wherein an inflation medium can be a fluid, such as a saline solution, contrast agent, or any other flowable material.

Expandable member 110 can be mounted to the distal end of an elongate member 130. Elongate member 130 is any structural component suitable for traversing the vasculature and having a distal and a proximal end with at least one lumen there through. For example, elongate member 130 can comprise a catheter or a plurality of catheters. In other embodiments, elongate member 130 can comprise a needle, e.g. a hypodermic needle. Elongate member 130 can be rigid or flexible.

In an embodiment, elongate member 130, as used herein, comprises an expandable lumen for purposes of expanding, inflating and/or everting expandable member. Elongate member 130 can also comprise an infusion lumen for purposes of infusing drug delivery component 120 with a fluid and ventilating drug delivery component 120. Elongate member can further comprise a ventilation lumen can be useful to purge air in drug delivery component 120 and to indicate to a clinician when a drug delivery component 120 has been infused. Elongate member 130 can be configured to be bendable to traverse through tortuous vasculature, and can further be configured to minimize or eliminate kinking. Elongate member 130 can comprise an inner diameter of sufficient size to permit passage of an inflation medium. Elongate member 130 can comprise any medical-grade material. Elongate member 130 can comprise polymeric or metallic materials or combinations thereof. For example, elongate member 130 can comprise a polymeric film tube with spiral or braided nitinol reinforcements.

Typical materials used to construct elongate member 130 can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenylene Ether (PPE), Modified Polyphenylene Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), expanded Polytetrafluoroethylene (ePTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

At the proximal end of elongate member 130, a hub 140 can be coupled thereto. Hub 140 can comprise any structural component suitable for facilitating introduction of an inflation medium into expandable member 110. For example, hub 140 can comprise an expansion port 141 in fluid communication with expandable member 110 via expansion lumen. In addition, in some infusible embodiments, hub 140 can further be configured to facilitate infusion and/or ventilation of drug delivery component 120. For example, hub 140 can comprise an infusion port 142 in fluid communication with drug delivery component 120 via an infusion lumen, and a ventilation port 143 in fluid communication with drug delivery component 120 via a ventilation lumen.

In an embodiment, with reference to FIGS. 2A to 2F, vascular drug delivery device 200 can comprise expandable member 210 and drug delivery component 220. Drug delivery component 220 can circumscribe, be situated about, and/or be mounted around inner expandable member 210. Drug delivery component 220 can be configured to deliver a therapeutic agent upon pressurization of the expandable member 210 to a pressure less than about 3 to about 20 psi. Drug delivery component 220 can be configured to be infused with a therapeutic agent, and can further be configured to be ventilated via a ventilation port. In some embodiments, device 200 can be configured to evert into position.

Expandable member 210 can comprise any inflatable device. Expandable member 210 can be any shape suitable to expand and substantially occupy the lumen at the treatment site. Expandable member 210 can be a generally compliant and/or bendable material to facilitate substantially occupying the vessel lumen along a length and further to enable eversion and expansion at low pressures, e.g., pressures about of 1 psi to about 10 psi above the ambient pressure. In an embodiment, expandable member 210 can have a generally tubular shape.

In addition, in various embodiments, expandable members can also be radially compliant thereby permitting device 200 being capable of expanding into a range of diameters. In addition, expandable members can be radially compliant across a length. In the instance of treating the entire length of a tapered lumen, as is often the case for the greater saphenous vein, device 200 can be capable of treating a lumen that varies in diameter across its length by about 5 mm, about 10 mm, or about 15 mm. For example, device 200 can treat a lumen that tapers from a diameter of about 10 mm to a diameter of about 5 mm.

In some embodiments, expandable member 210 can be liquid-tight or impermeable. In this manner, the lumen of expandable member 210 is not in fluid communication with drug infusible layer. In other embodiments, expandable member 210 can be permeable and/or be configured to permit a fluid to weep to its outer surface. The fluid weep-ability can facilitate the transfer of a therapeutic agent, e.g., by solvating or diluting the therapeutic agent.

In some embodiments, expandable member 210 can comprise a balloon. Balloon formation can be carried out in any conventional manner using known extrusion, blow molding and other molding techniques. Typically, three major steps in the process include extruding a tubular preform, molding the balloon and annealing the balloon. Depending on the balloon material employed, the preform can be axially stretched before it is blown. Techniques for balloon formation are described in U.S. Pat. No. 4,490,421 to Levy; RE32,983 to Levy; RE33,561 to Levy; and U.S. Pat. No. 5,348,538 to Wang et al., which are hereby incorporated by reference in their entireties.

The balloon can be attached to elongate member 230 by various bonding techniques known to the skilled artisan. Examples include, but are not limited to, solvent bonding, thermal adhesive bonding and heat shrinking or sealing. The selection of the bonding technique is dependent upon the materials from which the expandable element and tubular body are prepared. Refer to U.S. Pat. No. 7,048,713 to Wang, all of which is hereby incorporated by reference in its entirety.

According to the present disclosure, the balloon can be formed using any materials known to those of skill in the art with the desired physical properties. Commonly employed materials include the thermoplastic elastomeric and non-elastomeric polymers and the thermosets.

In various embodiments configured to evert, a thin, strong and impermeable version of PTFE membrane is useful because PTFE membranes possess a low coefficient of friction, are strong, and are very flexible, allowing device 200 to turn upon itself while everting. Expandable members made of PTFE can also be radially compliant.

Examples of suitable materials include but are not limited to, polyolefins, polyesters, polyurethanes, polyamides, polyether block amides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. For example, see U.S. Pat. No. 5,500,181, to Wang et al., which is hereby incorporated by reference, in its entirety. As used herein, the term "copolymer" shall be used to refer to any polymer formed from two or more monomers, e.g. 2, 3, 4, 5 and so on and so forth.

Useful polyamides include, but are not limited to, nylon 12, nylon 11, nylon 9, nylon 6/9 and nylon 6/6. The use of such materials is described in U.S. Pat. No. 4,906,244 to Pinchuk et al., for example, which is hereby incorporated by reference in its entirety. Examples of some copolymers of such materials include the polyether-block-amides, available from Elf Atochem North America in Philadelphia, Pa. under the tradename of PEBAX®. Another suitable copolymer is a polyetheresteramide.materials available for use are vast and too numerous to be listed herein and are known to those of ordinary skill in the art.

Suitable polyester copolymers, include, for example, polyethylene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth can be employed herein. Other styrenic block copolymers include acrylonitrile-styrene and acrylonitrile-butadienestyrene block copolymers. Also, block copolymers wherein the particular block copolymer thermoplastic elastomers in which the block copolymer is made up of hard segments of a polyester or polyamide and soft segments of polyether can also be employed herein. Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials which can be employed in balloon formation are further described in, for example, U.S. Pat. No. 6,406,457 to Wang et al.; U.S. Pat. No. 6,284,333 to Wang et al.; U.S. Pat. No. 6,171,278 to Wang et al.; U.S. Pat. No. 6,146,356 to Wang et al.; U.S. Pat. No. 5,951,941 to Wang et al.; U.S. Pat. No. 5,830,182 to Wang et al.; U.S. Pat. No. 5,556,383 to Wang et al.; U.S. Pat. No. 5,447,497 to Sogard et al.; U.S. Pat. No. 5,403,340 to Wang et al.; U.S. Pat. No. 5,348,538 to Wang et al.; and U.S. Pat. No. 5,330,428 to Wang et al., all of which are hereby incorporated by reference in their entireties.

The above materials are intended for illustrative purposes only, and not as a limitation on the scope of the present disclosure. Suitable polymeric materials available for use are vast and too numerous to be listed herein and are known to those of ordinary skill in the art.

In various embodiments, vascular drug delivery device 200 can comprise an inner expandable member 210 and an outer drug delivery component 220 wherein the drug delivery component 220 comprises a drug infusible layer 221 located on the outer surface of expandable member 210. Drug infusible layer 221 can be infused via infusion lumen 222. In accordance with specific embodiments, no therapeutic agent is present in drug delivery component 220 until drug delivery component 220 is in position for treatment. Once in position, a therapeutic agent can then be infused into drug delivery component 220. In addition to, drug delivery component 220 can comprise an outer barrier 225. Outer barrier 225 circumscribes, is mounted around, or is situated about infusible layer 221 and prevents the macroscopic transfer of a therapeutic agent until re-expansion of expandable member 210. Outer barrier 225 is described in further detail below.

In various embodiments, drug delivery component 220 can be configured to customize the amount of therapeutic agent released per unit area. For example, the infusion volume and/or saturation capabilities can be varied by varying the thickness and/or distensibility of infusible layer 221 and/or by selecting infusible layer 221 materials with desired saturation properties. In this manner, the therapeutic agent release volumes can be tailored. By tailoring to utilize an effective but minimum amount of therapeutic agent, costs as well as unwanted secondary effects could potentially be reduced.

Figure 2A:
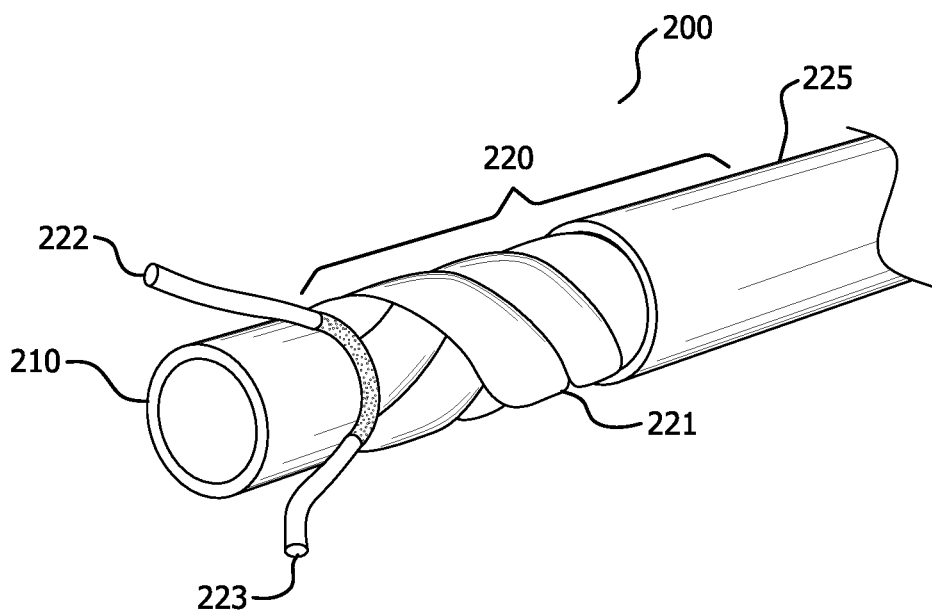
FIG. 2A illustrates a layered, cross-sectional view of a vascular drug delivery device.

In an embodiment, with reference to FIG. 2A, infusible layer 221 can comprise any material or structural configuration which facilitates distribution of a therapeutic agent throughout a majority or substantial portion of infusible layer 221. For example, infusible layer 221 can comprise a wicking material, a porous wall or layer, and/or a material that provides sufficiently low resistance to fluid flow. In addition, infusible layer can comprises a sufficiently crush resistant material so that it does not kink when extended across a tortuous vasculature. In an embodiment, infusible layer 221 can comprise a highly nodal, low-density or open pore membrane of PTFE such as that described in U.S. Pat. No. 5,814,405 by Branca et al. entitled "Strong, Air Permeable Membranes of Polytetrafluroethylene," which is hereby incorporated by reference in its entirety. FIGS. 2G-1 to 2G-2 illustrate a porous microstructure (at two scales of magnification) suitable for use in drug infusible layer 221. Other suitable materials can include open cell polyurethane foam, open cell silicone foam, open cell fluoropolymers, or any other pliable materials comprising micro or macro channels to allow infusion The material(s) utilized in infusible layer 221 can also be surface treated to vary the hydrophobic or hydrophilic properties of infusible layer 221. Such treatments can vary based on the therapeutic agent to be infused. In an embodiment, infusible layer 221 comprising ePTFE can be coated with polyvinylalcohol (PVA) to render layer 221 more hydrophilic.

Figure 2B:
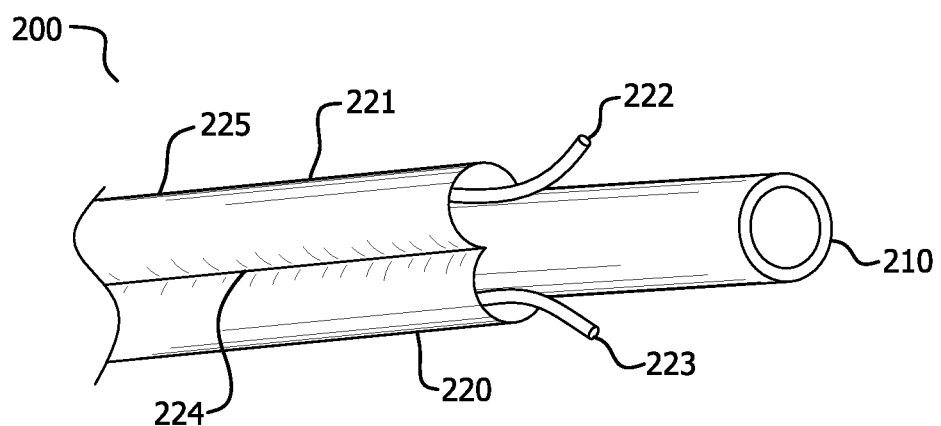
FIG. 2B illustrates a layered, cross-sectional view of a vascular drug delivery device.

In various embodiments, with reference to FIG. 2B, infusible layer 221 can comprise a film-like sleeve circumscribing the expandable member 210 and defining at least a portion of interstitial space, such interstitial space being the region to be at least partially filled with a therapeutic agent. To facilitate distribution of a therapeutic agent, an infusible layer 221 can comprise at least one seam 224 or a plurality of seams 224 which outlines an infusion path. In an embodiment, seam 224 can be a spiral shape. In other embodiments, drug infusible layer can comprise a plurality of seams 224 arranged in a substantially parallel manner.

In order to infuse, again with reference to both FIGS. 2A and 2B, device 200 can comprise an infusion lumen 222 that transports a therapeutic agent to infusible layer 221 via an inflation port. In order to ensure and facilitate distribution, drug delivery component 220 can further comprise a ventilation lumen 223, also in fluid communication with infusible layer 221.

Infusion lumen 222 and ventilation lumen 223 can be in fluid communication with infusible layer 221 at any location on infusible layer 221. In an embodiment, infusion lumen 222 is in fluid communication on a proximal end and ventilation lumen 223 is in fluid communication on a distal end, or vice versa. Embodiments can also comprise infusion lumen 222 in fluid communication at a first end of an infusion path and ventilation lumen 223 in fluid communication at a second end of the infusion path.

In an embodiment, infusion can occur prior to or after expansion of expandable member 210. Infusing while expandable member 210 is at a minimal or negligible pressure can enhance the degree of distribution of the therapeutic agent throughout infusible layer 221. Once infused, expandable member 210 can be expanded to occupy the lumen and facilitate the transfer of the therapeutic agent.

Figure 2C:
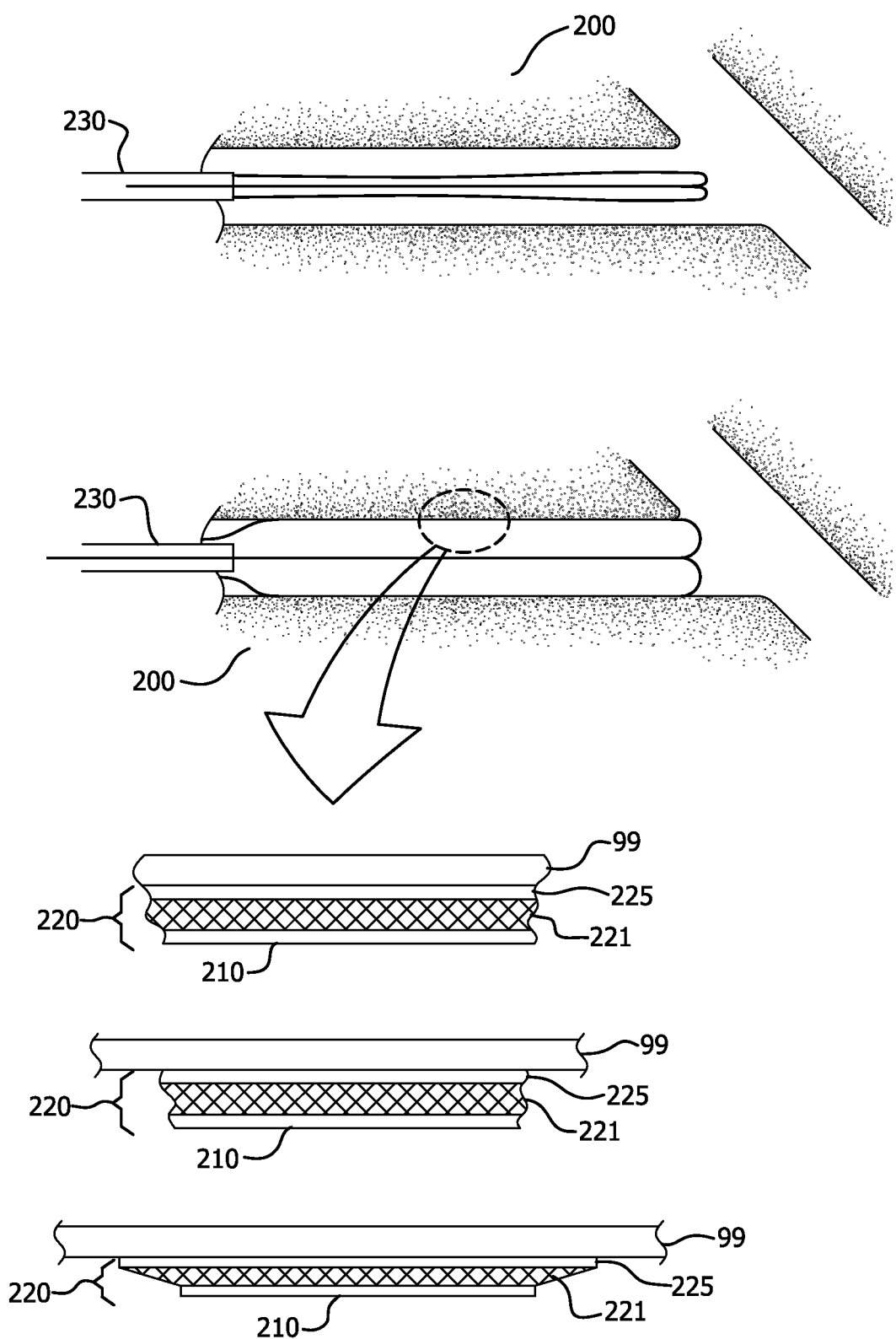
FIG. 2C illustrates side views of a vascular drug delivery device embodiment inserted into lumen of a vessel at a reduced pressure for drug infusion and at an increased pressure for drug delivery.

In addition, as referenced above, drug delivery component 220 can comprise outer barrier 225. Outer barrier 225 can partially or substantially block the transfer of an infused therapeutic agent until drug delivery component 220 is approaching or in close proximity to the surrounding tissue. In some embodiments, drug delivery component 220 can be configured to transfer the therapeutic agent across outer barrier 225 once expandable member 210 is pressurized above a specific pressure threshold. As expandable member 210 is pressurized and expanded (as illustrated in FIG. 2C), infusible layer 221 can be compressed between expandable member 210 and a vessel wall 99, causing transfer of the therapeutic agent to vessel wall 99.

Pressure thresholds can be as low as about 0.5 psi to about 20 psi above ambient pressure of the lumen. (Ambient pressure can be the normal pressure within the lumen, or in other embodiments where compression is to be applied to the surrounding tissue before and/or during a procedure, ambient pressure can be the pressure within the lumen under compression.) For example, outer barrier 225 can comprise any film or membrane material that does not permit macroscopic transfer of the therapeutic agent in a vein below a pressure of about 15 psi, about 5 psi, or about 3 psi and does permit such transfer above the threshold pressure. In an embodiment, outer barrier 225 can comprise a fluoropolymer film, e.g., a PTFE film. Other suitable film materials include polyurethane, polyester, PEBAX and other nylons, PVC, PVDF, polyethylene, and or other biocompatible polymer used in medical applications.

In other or the same embodiments, outer barrier 225 can be configured to transfer the therapeutic agent upon radial expansion, which alters the permeability of the microstructure of outer barrier 225. In an embodiment, outer barrier 225 material can comprise a fibrillated structure, such as expanded fluoropolymers (e.g., ePTFE) or polyethylene, fibrous structures (such as woven or braided or non-woven mats of fibers, microfiber, or nanofibers), or films with openings created during processing (such as laser or mechanically drilled holes or foams or microporous membranes, etc.). In another embodiment, the material comprises micropores between nodes interconnected by fibrils, such as in ePTFE. In another embodiment, the material comprises micropores in an essentially nodeless ePTFE, as described in U.S. Pat. No. 5,476,589 to Bacino, which is hereby incorporated by reference in its entirety.

Outer barrier 225, on its outer surface, can be modified with textures, protrusions, depressions, grooves, coatings, particles, and the like. These can serve various purposes such as to modify tissues into which therapeutic agents will be (or have been) delivered, control placement of the system of the disclosure, and direct fluid transfer. In another embodiment, outer barrier 225 can contain or be marked with radiopaque markers or be constructed to be radiopaque in its entirety. To properly track and place vascular drug delivery device 200, clinicians can use such radiopaque indicators.

To further control the delivery of a therapeutic agent, outer barrier 225 can comprise sections or areas that remain impermeable to the therapeutic agent throughout the treatment process. For example, having an impermeable end cap(s) can further mitigate undesired migration of the agent. Areas of outer barrier 225 can be made impermeable by coating or imbibing with polyurethane, silicone, or any other material that can render the outer barrier 225 impermeable where applied.

Figure 2D:
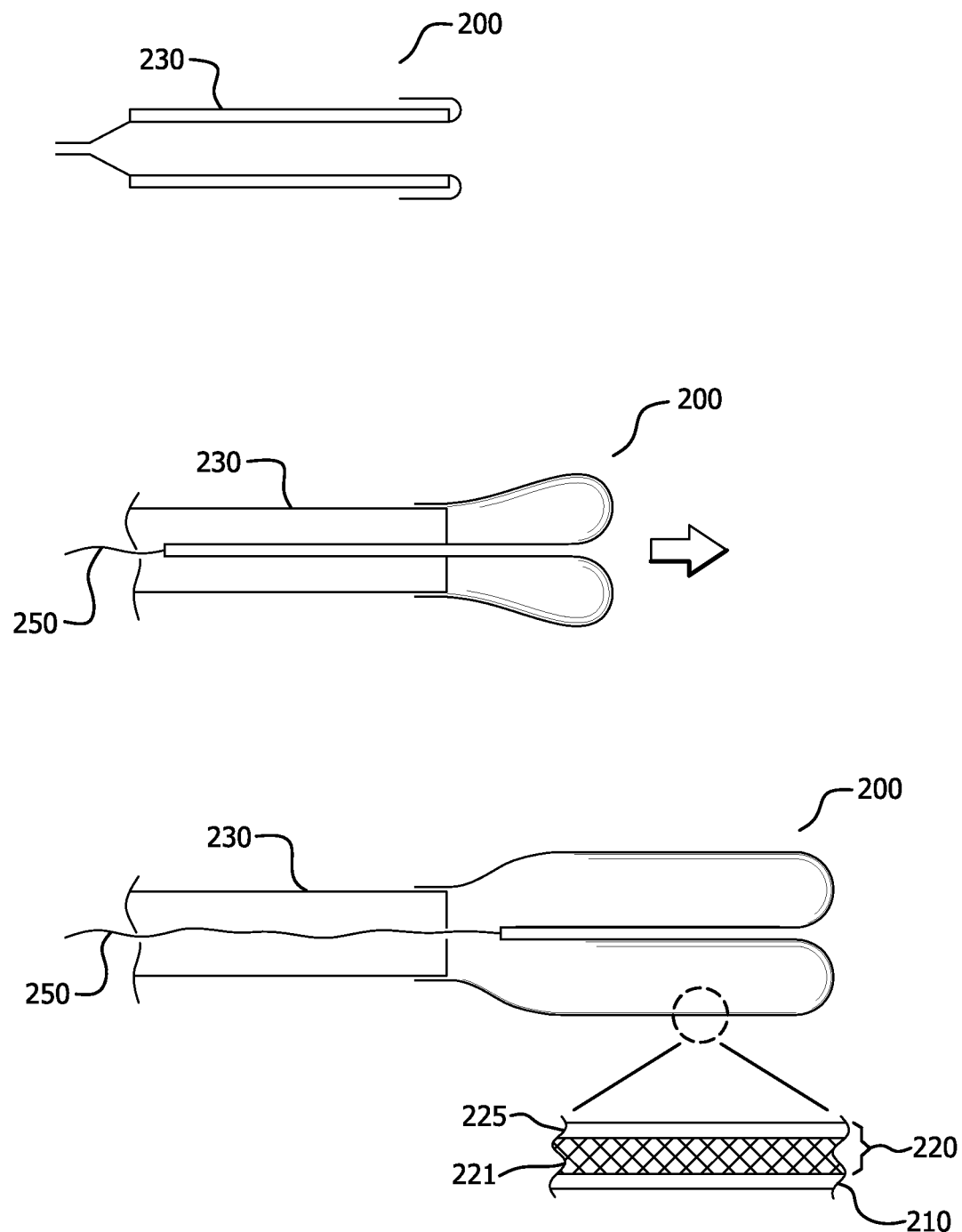
FIG. 2D illustrates side views of a vascular drug delivery device embodiment retracted within lumen of elongate member and then extending outward as the expandable member is pressurized.
Figure 2E:
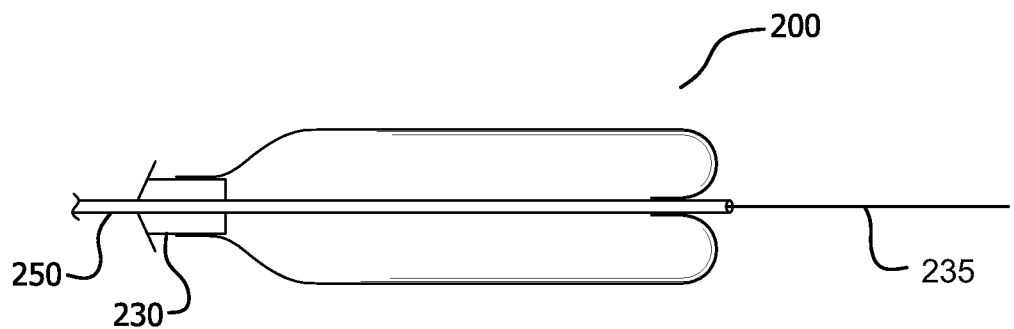
FIG. 2E illustrates a side view of a vascular drug delivery device embodiment configured to traverse along a guidewire.

In some embodiments, with reference to FIG. 2D, vascular drug delivery device 200 can comprise an inner expandable member 210 and an outer drug delivery component 220 which can extend and retract through the lumen of a vessel by eversion. Everting permits expandable member 210 and drug delivery component 220 to extend through and substantially occupy a lumen, even a tortuous lumen, e.g. a saphenous vein, along lengths up to and greater than 200 cm. Expandable member 210 and drug delivery component 220 together can form a layered tubular member, wherein expandable member 210 is a base layer and drug delivery component 220 is a surface layer that covers at least a section of the expandable member 210. The proximal end of layered tubular member can be mounted on the distal end of elongate member 230. In an extended configuration, drug delivery component 220 is located about the outer surface of expandable member 210 and both extend from the end of elongate member 230. In the initial position, expandable member 210 and drug delivery component 220 can be folded or longitudinally compressed about elongate member 230 or retracted within lumen of elongate member 230 (as illustrated in FIG. 2C). Upon pressurization of expandable member 210, expandable member 210 and drug delivery component 220 can evert and/or extend through the lumen of a vessel or the like. In some embodiments, with reference to FIG. 2D, the distal end of layered tubular member can be sealed and can extend into lumen unguided. In other embodiments, with reference to FIG. 2E, a distal end of the layered tubular member can be coupled to a distal end of second elongate member 235, which is slideable with the lumen of elongate member 230.' This embodiment can facilitate extending along a path provided by a guidewire.

Once expandable member 210 and drug delivery component 220 are in the desired location, the position of the components can be fixed to prevent further extension. To facilitate fixation, device 200 can further comprise a length fixation mechanism, i.e., a mechanism to prevent further extension of device 200 once desired location is reached. For example, length fixation mechanism can comprise a tethering device 250, such as a tube, guidewire, filament, thread, or the like coupled to the distal end of expandable member 210. Tethering device 250 can slideably extend from the distal end of expandable member 210 to the proximal end of device 200. In some embodiments, tethering device 250 can extend through inflation lumen. During a treatment procedure, once the device is located along the treatment area, the proximal end of tethering device 250 can be secured, and thereby, the length of expandable member 210 and drug delivery component 220 can be fixed. Other length fixation mechanisms can comprise a clamp, a fastener, or the like which secures a proximal section of expandable member 210 and/or drug delivery component 220 to elongate member 230, thereby preventing further extension.

Once the therapeutic agent has been delivered to the surrounding tissue, expandable member 210 and drug delivery component 220 can be collapsed and then retracted. To facilitate retraction, tethering device 250 can be pulled and the expandable member 210 and drug delivery component 220 can evert into the lumen of expandable member 210 and eventually into the lumen of elongate member 230. Optionally, tethering device 250 can be twisted and pulled during re-eversion to retract. Another mode of retraction can include simply pulling, or twisting and pulling, in the proximal direction on the proximal end of elongate member 230. In an embodiment, retraction of expandable member 210 and drug delivery component 220 can be conducted in conjunction with extrinsic manipulation (e.g., manual compression) of the treated tissue.

Figure 2F:
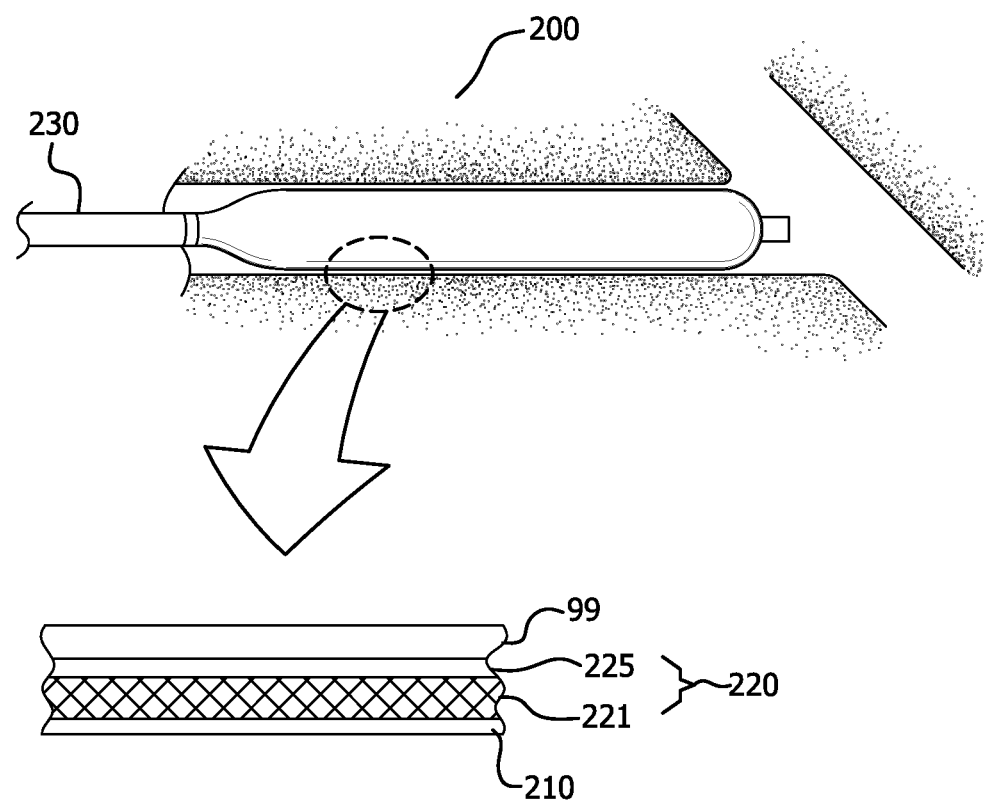
FIG. 2F illustrates a side view of a non-everting vascular drug delivery device embodiment mounted on the end of elongate member.
Figures 1, 2G:
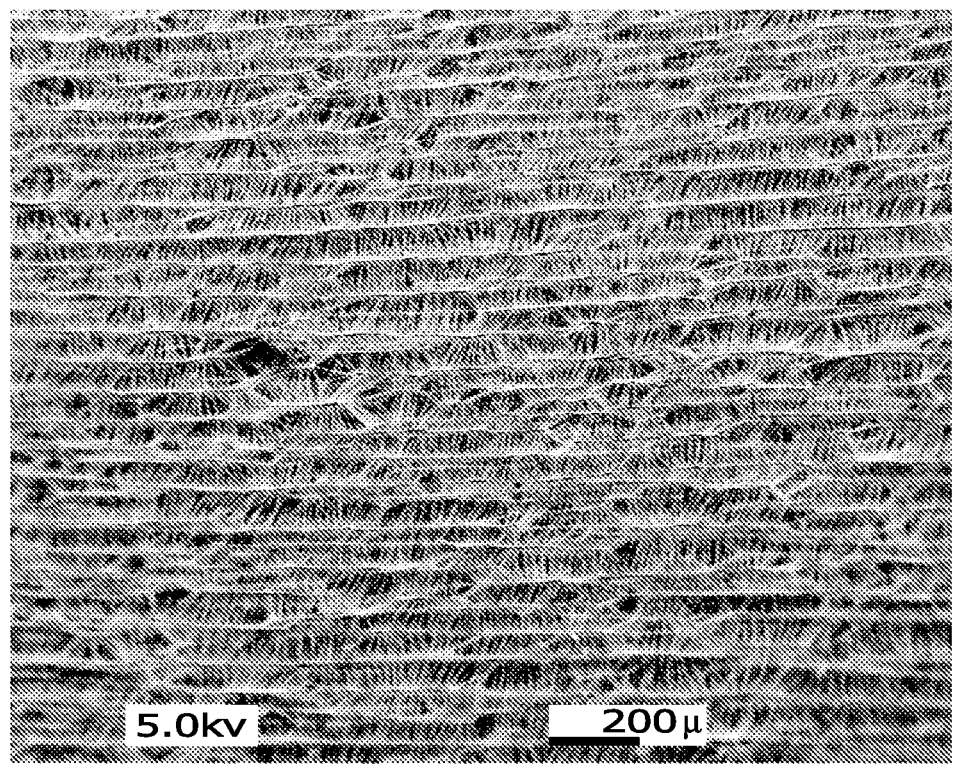
FIGS. 2G-1 to 2G-2 provide two variously scaled illustrations of a porous microstructure suitable for use in the drug infusible layer.
Figures 2, 2G:
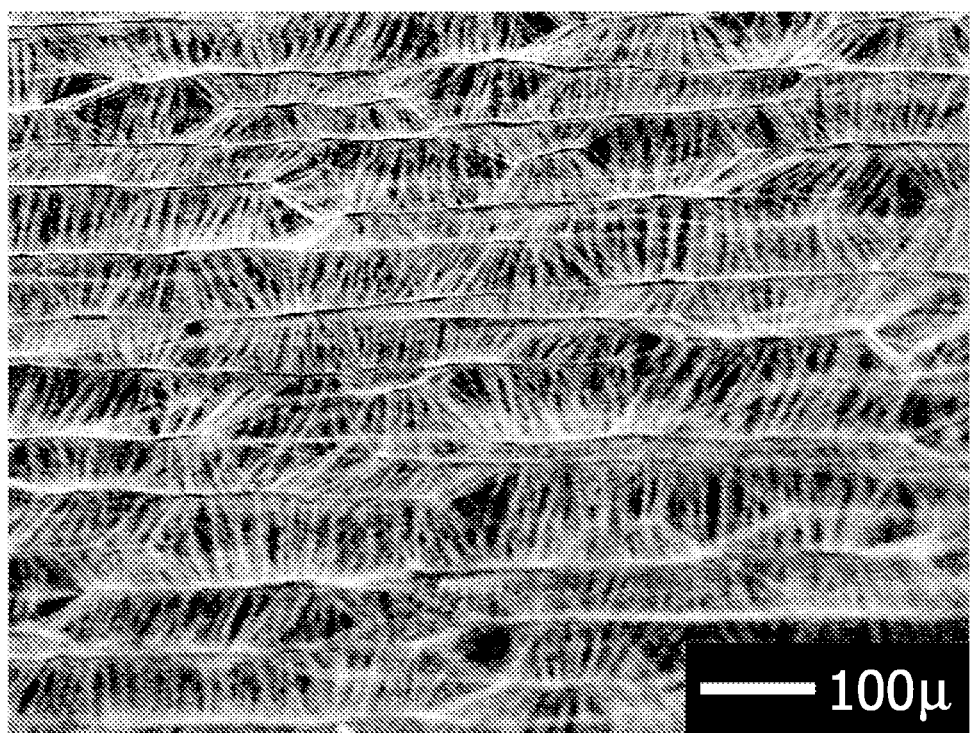

In an alternative configuration, with reference to FIG. 2F, vascular drug delivery device 200 can comprise inner expandable member 210 and outer drug delivery component 220 mounted on a distal portion of elongate member 230. Elongate member 230 extends through the length of the lumen to be treated. Once in position, drug delivery component 220 can be infused and expandable member 210 can be pressurized.

In accordance with another embodiment, a method of delivery can comprise the steps inserting drug delivery device 200 into a vessel; advancing to a location proximate the treatment site; and everting expandable member 210 and drug delivery component 220 by increasing the pressure within expandable member 210. Pressure can be increased by injecting an inflation medium into expandable member 210. During eversion, the compliant layered tubular combination of drug delivery component 220 and expandable member 210 will advance along the path of least resistance, thereby avoiding any minor side branches.

Once drug delivery component 220 is extended along the desired treatment site, reduce the pressure within expandable member 210; e.g., reduce the pressure to a minimal or negligible pressure; and secure proximal end of tethering device 250. Securing tethering device 250 will "lock" the length of device 200, i.e., not allow further eversion during subsequent pressurizations.

A further step can comprise infusing a therapeutic agent into drug infusible layer 221. During injection of the therapeutic agent, the agent can displace any air entrapped in drug infusible layer 221; this air can be expelled through ventilation lumen 223 and exit the ventilation port located on the hub. Once a drop of therapeutic agent exits the ventilation port, the clinician can be sure that drug infusible layer 221 is substantially infused or full. Upon observing a certain amount of the therapeutically agent exiting the ventilation port, the infusion and ventilation ports can be closed.

Another step can comprise increasing the pressure within expandable member 210. Increasing pressure within expandable member 210 will apply pressure to drug infusible layer 221 and outer barrier 225. When a pressure threshold is exceeded, outer barrier 225 will begin to allow trans-mural perfusion of the therapeutic agent. In this manner, the agent can be delivered directly to the surrounding tissue.

Additional steps can comprise slightly reducing the pressure within the expandable member 210 an amount to permit device 200 to evert into elongate member 230 and applying tension to tethering device 250. Tension applied to tethering device 250 will force device 200 to evert back within itself, and ultimately, back within the elongate member 230. As device is re-everted, i.e., retracted, the inflation medium within expandable member 210 will be slowly forced out of the unlocked expansion port.

A further step can require repeating the aforementioned steps because once expandable member 210 and drug deliver component 220 are completely retracted, elongate member 230 can be repositioned and the procedure can be repeated. Once the therapy is complete, elongate member 230 can be removed from the vasculature.

In the above described method of delivery, it is contemplated that compression to the surrounding tissue can be applied before, during, and/or after a treatment procedure. Compression, which reduces the volume of the lumen, can be applied across the length of the lumen. For example, in the case of a treatment procedure involving an arm or a leg, such as a saphenous vein treatment, compression socks or the like can be utilized. In addition, the tissue can be monitored with non-invasive imaging, e.g., ultrasound to assess the efficacy of the treatment.

In another aspect of the present disclosure, an occluding device comprises a bioabsorbable, lumen-occluding implant, which can optionally be imbibed with a therapeutic agent. Bioabsorbable, lumen-occluding implants (also referred to herein as "bioabsorbable implants") comprise an implant made of a bioabsorbable material that has an occlusive effect. In some embodiments, the bioabsorbable implant can expand to occupy a width or cross-section approximately the width of the lumen or body cavity to be occluded. In the same or different embodiments, based on the selection of the bioabsorbable material or the therapeutic agent, the bioabsorbable implant can cause a thrombogenic response to form an occlusion and/or a spasmodic response to form an occlusion by causing the surrounding tissue to shrink or collapse around the implant. To facilitate the occlusive effect, manual compression techniques about the surrounding tissue to collapse and/or reduce to volume of the lumen can be utilized. In some embodiments, bioabsorbable implants have lengths which extend along a length of a lumen and/or conform to the shape of the lumen.

Bioabsorbable, lumen-occluding implants can be useful for the treatment of saphenous vein incompetency, endoleaks, perivalvular leaks, patent ductus, patent foramen ovale, aortic dissection, growing aneurysms, gastro-esophageal reflux, and obesity (by shrinking the gastro-esophageal junction or pylorus), tumors, or any disease or condition where local drug delivery and/or an occlusive or spasmodic effect is desired. Some embodiments could be used as an alternative to tubal ligation or vasectomies, and embodiments causing a spasmodic response could also be useful in cosmetic wrinkle reduction applications.

Embodiments herein can be adapted for use in cell based therapy such as cell seeding. Embodiments can be imbibed with cells and further imbibed with nutrients and/or other therapeutic agents.

Further embodiments described herein include systems or kits comprising a bioabsorbable implant and a delivery device. In some embodiments, delivery devices comprise an implantation guide which facilitates delivery of the bioabsorbable implant or a bioabsorbable implant component to an implantation site by providing a delivery path. In other embodiments, delivery devices comprise an implantation guide and a translating member, wherein the translating member facilitates translation of the bioabsorbable implant along the delivery path defined by the implantation guide. Translating member embodiments include a syringe, an implantation piston member, or any other device that facilitates translation of the bioabsorbable implant along the delivery path.

Bioabsorbable lumen-occluding implants describe herein can comprise any shape suitable for introduction into a lumen. For example, in occluding a lumen, bioabsorbable implant can comprise any space-filling member with a generally round or polygonal cross-section such as a spherical, ovoidal, cylindrical, ellipsoidal or prismoidal shape, or combinations and/or repetitions of the foregoing. Bioabsorbable implant can have a generally open framework or a hollow center, or alternatively, it can be generally solid. In addition, in some embodiment, bioabsorbable implants can comprise a generally elongated dimension, i.e., having a greater length than width or height. Bioabsorbable implants can be made to be permeable and/or can also be fashioned into bioabsorbable conduits through which a therapeutic agent can be infused.

In an embodiment, the bioabsorbable implant can be configured to conform approximately to the dimensions of the lumen to be occluded. In the same or different embodiments, the bioabsorbable implant can facilitate the surrounding tissue conforming to the dimensions of the bioabsorbable implant, such as through the use of therapeutic agents like spasmodic agents, pro-coagulants, and/or biocompatible glues/tissue adhesives, as well as manual compression.

Bioabsorbable, lumen-occluding implants describe herein can optionally be imbibed or infused with a therapeutic agent and/or comprise a modified outer surface to have an improved or additional bioactive response. In an embodiment, modifying the surface can comprise any modification that increases the surface area of the bioabsorbable implant. In some embodiments, surface modifications can enhance the thrombogenic response caused by bioabsorbable implant. One modification comprises adhering small fiber particles to at least a portion of the surface of bioabsorbable implant, creating an at least partially flocked surface. These small fiber particles can also be bioabsorbable. Another modification can comprise an abraded or roughened surface.

Bioabsorbable elements referred to herein, namely, bioabsorbable, lumen-occluding implants, anchoring mechanisms, radiopaque markers, occlusive material, and occlusive members, comprise bioabsorbable material(s). Bioabsorbable materials, as used herein, comprise any material capable of biological absorption. Such materials include copolymers of lactic acid and glycolic acid (PLA/PGA) adjusted in the desired ratio to achieve the desired rate of biological absorption. Other potentially useful bioabsorbable materials include polyglycolic acid (PGA), poly-L-lactic acid (PLA), polydiaoxanone (PDS), polyhydroxybutyrate, copolymers of hydroxybutyrate and hydroxyvalerate, copolymers of lactic acid and E-caprolactone, oxidized regenerated cellulose and various forms of collagen. A most preferred material is polyglycolide: trimethylene carbonate tri-block copolymer (PGA:TMC), e.g., the non-woven, bioabsorbable web material described in U.S. Pat. No. 7,659,219 by Biran et al. entitled "Highly porous self-cohered web materials having hemostatic properties," which is hereby incorporated by reference in its entirety. This material has a history of use as bioabsorbable sutures; it is described in detail by U.S. Pat. No. 4,429,080 to Casey et al., which is hereby incorporated by reference in its entirety. The proportions of this or any other selected copolymer or blends of polymers can be adjusted to achieve the desired absorption rate. Other potentially useful bioabsorbable, non-autologous materials including porous forms are described by U.S. Pat. No. 4,243,775 to Rosencraft et al.; U.S. Pat. No. 4,300,565 to Rosencraft et al.; U.S. Pat. No. 5,080,665 Jarrett et al.; U.S. Pat. No. 5,502,092 Barrows et al.; U.S. Pat. No. 5,514,181 to Light et al. and U.S. Pat. No. 5,559,621 to Minato et al., and published PCT application WO 90/00060 to Chu et al., all of which are hereby incorporated by reference in their entireties.

Implantation guide, referred to herein, can comprise any tubular member or hollow needle having a lumen through which an occluding device can pass through to be implanted into a lumen. In some embodiments, the implantation guide can be sufficiently flexible to extend along or traverse a curved or tortuous section of vasculature. In other embodiments, implantation guide does not need to extend along a curved or tortuous section of vasculature and thus, flexibility is not required.

The bioabsorbable implant embodiments described herein can further comprise bioabsorbable radiopaque markers to facilitate monitoring of the bioabsorbable implant in situ with non-invasive imaging techniques (e.g., ultrasound imaging). For example, markers can be mounted on a proximal and/or distal end of the implant. In an embodiment, markers may be useful to ensure the device is properly positioned at a vessel junction.

Figure 3A:
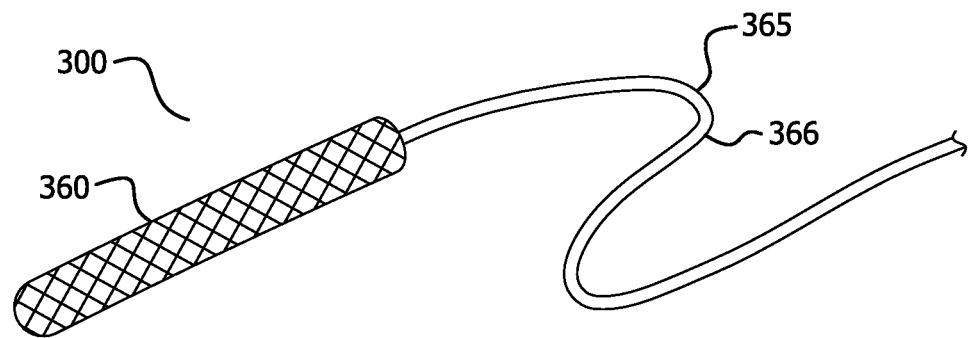
FIG. 3A illustrates an occluding device embodiment.
Figure 3B:
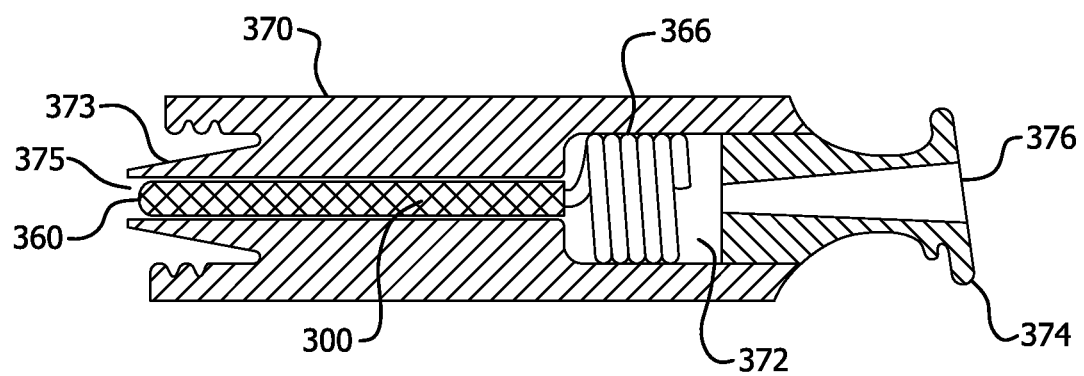
FIG. 3B illustrates a cross-sectional view of a pre-loaded delivery capsule embodiment.

In one embodiment, with reference to FIG. 3A, an occluding device 300 comprises a bioabsorbable, lumen-occluding implant 360 having an anchoring mechanism 365 coupled thereto. Anchoring mechanism 365 is any device suitable for maintaining the position of the bioabsorbable implant 360 in situ. For example, when implanted into a blood vessel for purposes of creating a permanent occlusion, the flow of blood should not dislodge the bioabsorbable implant 360. Anchoring mechanisms 365 can include a barb, a suture line 366, stent, or the like. Anchoring mechanism 365 can be coupled to implant at a proximal or distal end of implant 360 or any other suitable location on implant 360.

In one embodiment, occluding device 300 comprises a bioabsorbable, lumen-occluding implant 360 securely coupled to bioabsorbable suture line 366. Suture line 366 can be any length sufficient to extend from implant 360 to a point where suture line 366 can be secured, such as through the insertion path to the skin surface. A first end of suture line 366 can be securely coupled to bioabsorbable implant 360 at a proximal or distal end of bioabsorbable implant 360 or any other suitable location on implant 360. In an embodiment where suture line 366 exits the surface of the skin, suture line 366 can be knotted or, taped or cut flush with the surface of the skin.

In another embodiment, an occluding device 300 comprises a bioabsorbable, lumen-occluding implant 360 coupled to at least one bioabsorbable barb, hook, or stent (collectively referred to as "barb). Barb can be any structural component that can penetrate a tissue making it difficult to become naturally dislodged from the implantation site. In an embodiment, barb can be self-setting such that as implant 360 is inserted or injected into position, the barb will radially extend away from implant 360 and into surrounding tissue. The barb can be coupled to implant 360 at a proximal or distal end of the implant or any other suitable location on implant 360. In an embodiment, at least a portion of the barb can be oriented to generally curve, point or extend in the direction of blood flow to facilitate engagement with the surrounding tissue.

With reference to FIG. B and FIGS. 3C-1 to 3C-5, bioabsorbable implant 360 can be pre-loaded into a capsule 370. The pre-loaded device capsule 370 can be designed to connect to a syringe 382 and an implantation guide 380. With the use of the syringe 382, capsule 370 and syringe 382 can be filled with a delivery fluid (such as saline or a therapeutic agent solution). With the use of implantation guide 380 (and optionally, an ultra sound device), access is gained to the implantation site, e.g., the lumen of a vessel. Once implantation guide 380 is in position, capsule 370 and syringe 382 are connected to implantation guide 380. The plunger of the syringe 382 can then be depressed causing occluding device 300 to be implanted and anchored into position.

In various embodiments, pre-loaded device capsule 370 comprises a housing 371 defining at least one delivery chamber 372 in which at least one occluding device 300 as described above is oriented for delivery. Delivery chamber 372 is any pass-through cavity or compartment within housing 371 of appropriate dimensions for storing occluding device 300 in position for expulsion. As a pass-through, chamber 372 has an entrance end 376 and an exit end 375.

In order to connect to implantation guide 380 and syringe 382, housing 371 comprises connectors 373, 374, such as a Luer taper fitting, about each end 375, 376. For example, housing 371 can comprise a male-taper fitting about exit end 375 for connecting to implantation guide 380. About entrance end 376, housing 371 can comprise a female taper fitting for connecting to syringe 382. Device capsule 370 can further be hygienically sealed to maintain a sterilized delivery chamber 372 and occluding device 300. The caps or seals can be fitted onto the connectors 373, 374 and can be removed or disrupted at the time of use.

In various embodiments, pre-loaded device capsule 370 can be configured to receive an imbibing fluid containing at least one therapeutic agent. In this manner, occluding device 300 contained therein can be imbibed with a therapeutic agent moments prior to implantation. In an embodiment, delivery capsule 370 can comprise a pressure imbibing port and be configured to withstand positive pressures. The delivery chamber 372 can be filled with an imbibing fluid, liquid and/or gas, and held under positive pressure.

In other embodiments, pre-loaded device capsule 370 can comprise a plurality of delivery chambers 372 configured to revolve, such as with the aid of a ratchet device. Each delivery chamber 372 is loaded with occluding device 300 as described above. Such embodiments can help streamline the process of implanting multiple occluding devices 300 in a single treatment procedure. For example, in occluding a length of a vessel, a plurality of device can be implanted to align end to end as illustrated in FIG. 3C-5. In a further embodiment, pre-loaded device capsule 370 can comprise a pressure imbibing port for purposes of simultaneously imbibing a plurality of occluding devices 300.

In accordance with another embodiment, an implant kit can comprise (i) implantation guide 380 having a lumen through which occluding device 300 as described above can pass through; (ii) pre-loaded device capsule 370 as described above, and (iii) at least one syringe which facilitates the expulsion of at least one occluding device 300 from chamber 372 through the lumen of implantation guide 380 out of distal tip. In an embodiment, a distal end of implantation guide 380 can comprise an angled-cut tip and/or have a generally arced profile to facilitate placement of occluding device 300. Syringe 382 can be manually operated or be operated through automation.

Figures 1, 3C:
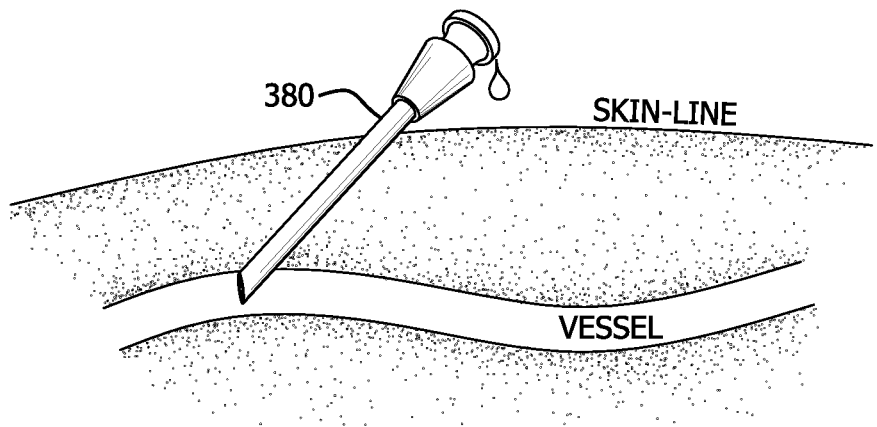
Figures 2, 3C:
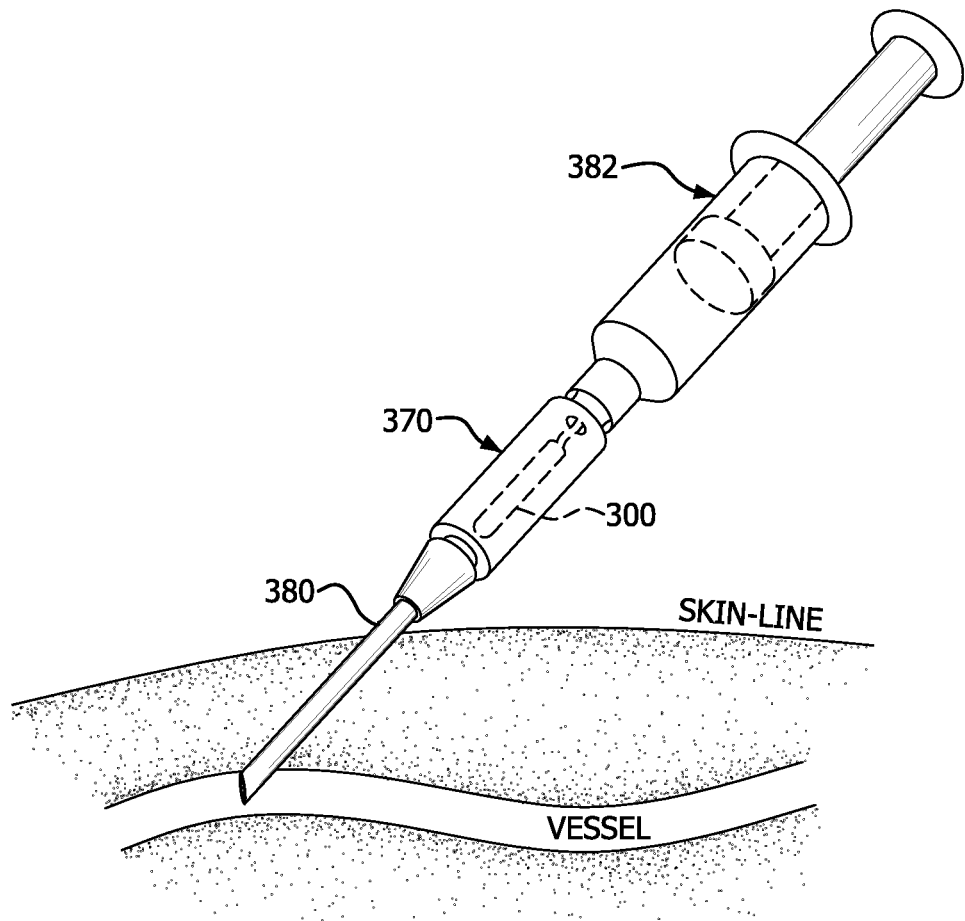
Figures 3, 3C:
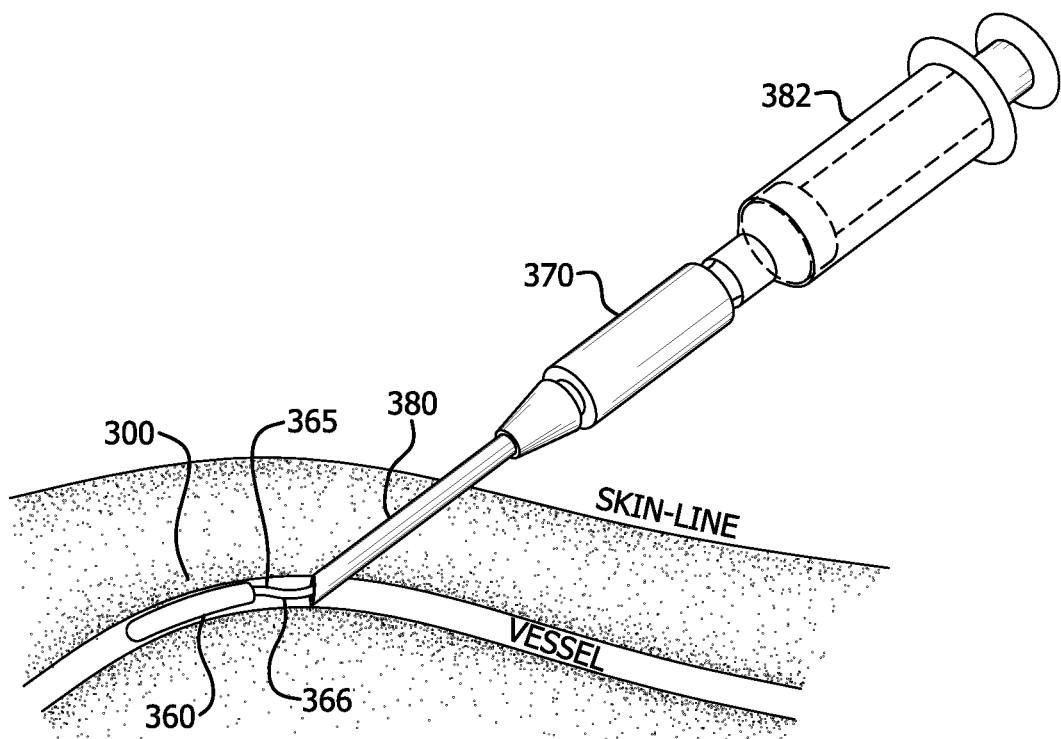
Figures 3, 3C, 4:
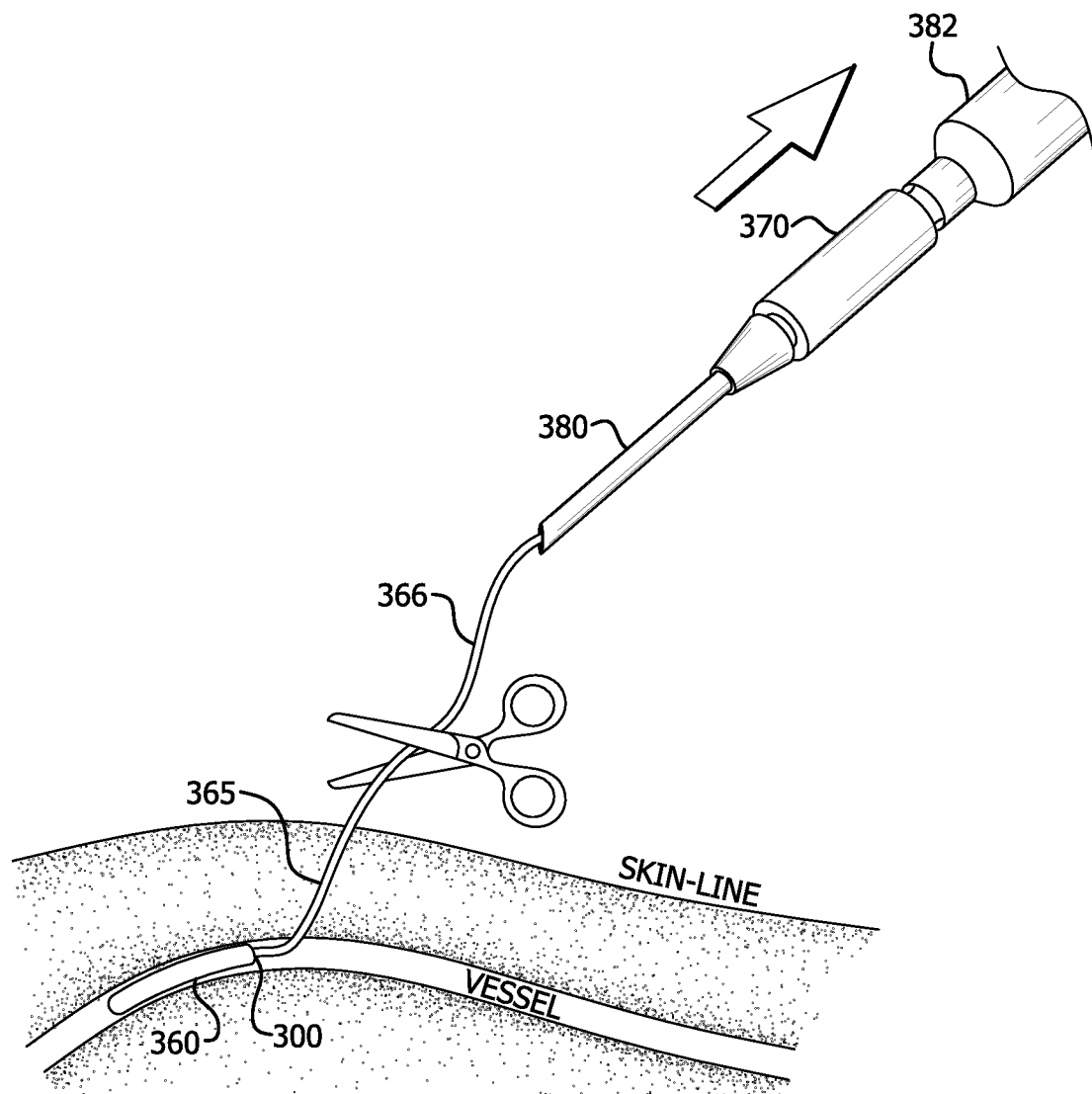

In accordance with another embodiment, a method of delivery can comprise the following steps. In any particular order, a clinician can connect syringe 382 to pre-loaded device capsule 370 and insert implantation guide 380 into the lumen of a vessel (FIG. 3C-1). Placement of implantation guide 380 can be guided with the use of an ultrasound device. Once implantation guide 380 is in position, pre-loaded device capsule 370 is fitted onto implantation guide 380 (FIG. 3C-2). Bioabsorbable implant 360 can then be expulsed through implantation guide 380 via the depression of syringe 382 plunger (FIG. 3C-3). Anchor mechanism 365 is then deployed (FIG. 3C-1).

In an embodiment where anchor mechanism 365 comprises suture line 366, suture line 366 remains within lumen of implantation guide 380, so upon retraction of implantation guide 380, suture line 366 extends along the insertion path to the surface of the skin. Suture line 366 can then be cut flush with skin, taped down, and/or knotted.

Implantation guide can be withdrawn and the aforementioned steps can be repeated at a neighboring location to implant a plurality of occluding devices 300 (FIG. 3C-5).

In another embodiment, with reference to FIGS. 4A-1 and 4A-2, and FIGS. 4B-1 TO 4B-2 an occluding device 400 comprises bioabsorbable, lumen-occluding implant 460 having a generally conformable conformation 461 when loaded into implantation guide 480 and a convoluted conformation 462 when released from implantation guide 480. Convoluted conformation 462 can comprise coiled or spiral configuration, an undulating configuration, and/or a more random configuration of bends, twists, or whorls configuration.

In accordance with another aspect of the disclosure, with reference to FIGS. 4A-1 to 4A-2 and FIGS. 4B-1 to 4B-2, an occluding device and delivery device system comprises implantation guide 480 circumscribing an extendable and retractable implantation piston member 496; and bioabsorbable lumen-occluding implant 460 having a generally conformable conformation 461 when loaded into implantation guide 480 and a convoluted conformation 462 when released from guide 480, wherein bioabsorbable lumen-occluding implant 460 can be releasably coupled to implantation piston member 496.

Implantation piston member 496 can comprise an elongated component that passes through the lumen of implantation guide 480 and releasably couples to occluding device 400. In an embodiment, implantation piston member 496 comprises an outer tube 497 with a translatable inner core 498 located within and along the lumen of outer tube 497. Implantation piston member 496 has a recessed distal end by way of outer tube 497 extending beyond translatable inner core 498 a certain distance. Along this distance or a portion thereof, outer tube 497 is dimensioned to fit snugly over occluding device 400 Outer tube 497 is also dimensioned to slideably extend and retract through implantation guide 480. In this manner, occluding device 400 can be loaded into implantation guide 480 and then it can be retracted and extended until occluding device 400 is released.

In order to release, translatable inner core 498 can be actuated to slide and extend within the lumen of outer tube 497 so that it is at least flush with the distal end of outer tube 497. In this manner, occluding device 400 is forced out of the lumen of outer tube 497 and released from implantation piston member 496.

In accordance with another embodiment, a method of loading occluding device 400 into implantation guide 480 comprises the steps of inserting a proximal end of occluding device 400 into a distal end of implantation piston member 496; retracting implantation piston member 496 and occluding device 400 into implantation guide 480 lumen.

In accordance with another embodiment, a method of delivery can comprise the following steps. First, implantation guide 480 is inserted into lumen. Once in position, implantation piston member 496 can be selectively extended so that occluding device 400 is released from implantation guide 480 and acquires a convoluted conformation 462. If desired, occluding device 400 can be again retracted into the lumen of implantation guide 480 by retracting implantation piston member 496. The steps of extending and retracting occluding device 400 can be repeated until occluding device 400 is in the desired implantation position. Once in the proper position, occluding device 400 can be released by actuating implantation piston member 496. For example, actuating implantation piston member 496 can comprise sliding and extending translatable inner core 498 along the lumen of the outer tube 497.

Figures 1, 4A:
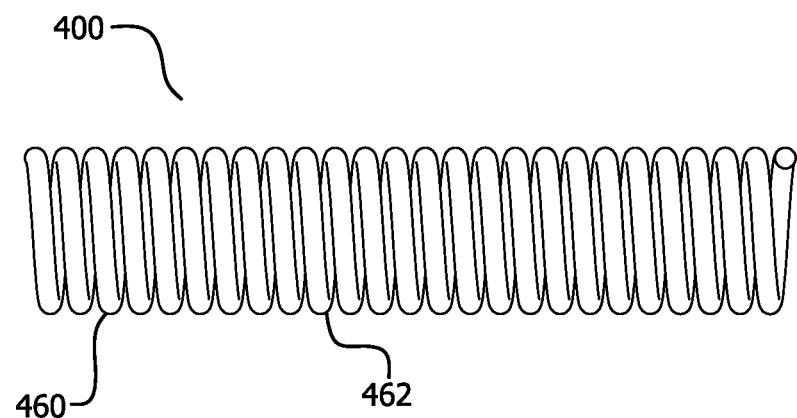
Figures 2, 4A:
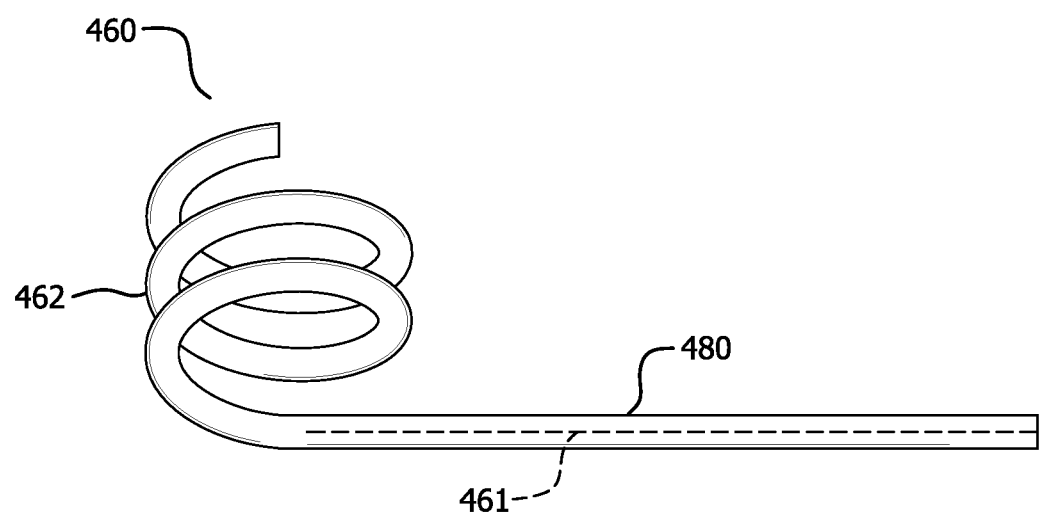
Figures 1, 4B:
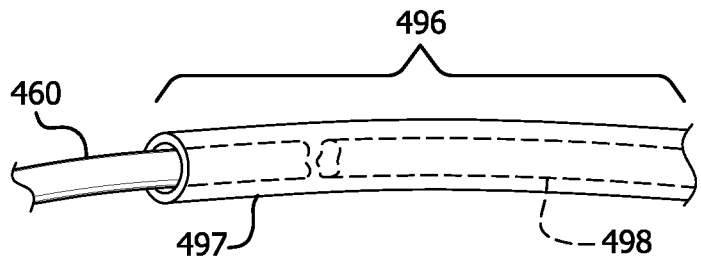
Figures 2, 4B:
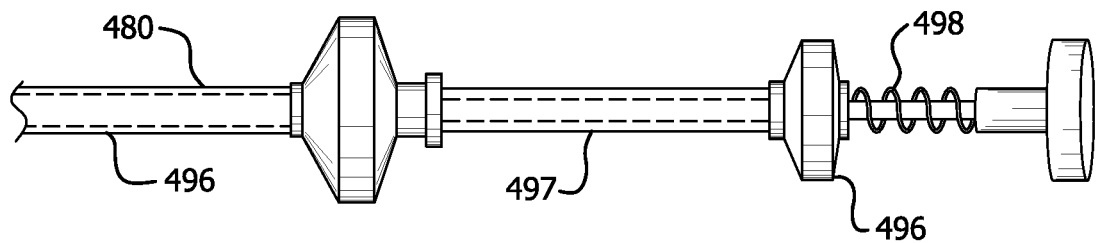
Figures 1, 4C:
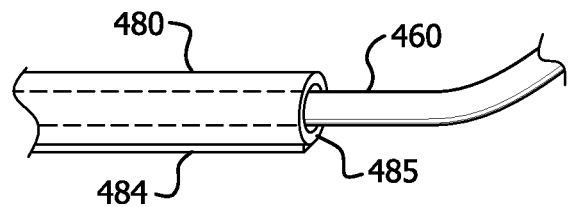
Figures 2, 4C:
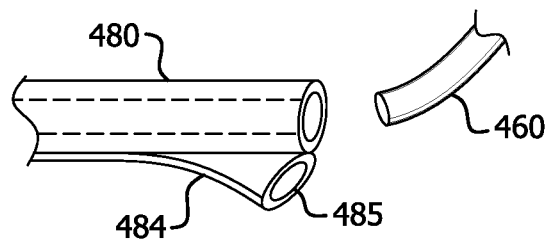

In an embodiment, with reference to FIGS. 4C-1 to 4C-2, occluding device and delivery system comprises a implantation guide 480, an actuatable cutter mechanism 484, and a bioabsorbable implant 460 having a conformable conformation 461 when loaded into guide 480 and a convoluted conformation 462 when released from guide 480, wherein the bioabsorbable implant 460 can be selectively extended and retracted, and then selectively severed with cutter mechanism 484 after a sufficient length of bioabsorbable implant 360 is implanted. Similarly, in an embodiment, occluding device and delivery system comprise guide 480, a cutter mechanism 484, and a bioabsorbable implant 460 having a customizable length.

In order to sever bioabsorbable implant 460, cutter mechanism 484 can comprise a blade 485 located on a distal end portion of implantation guide 380 and an actuating component extending from the blade 485. Blade 485 can be oriented so that the cutting edge faces toward the center of implantation guide 480 lumen. Upon actuation, blade 485 moves across implantation guide 480 lumen and can optionally reset itself. Blade 485 can comprise any material of suitable hardness to cut bioabsorbable implant 460. Blade 485 can be a hard polymer or a metallic component. Blade 485 can comprise a shape memory material, such as nitinol.

In an embodiment, with reference to FIGS. 4C-1 to 4C-2, an occluding device and delivery system comprise implantation guide 480, an actuatable cutter mechanism 484, and a bioabsorbable implant 460 having a conformable conformation 461 when loaded into guide 480 and a convoluted conformation 462 when released from guide 480, wherein the bioabsorbable implant 460 can be selectively extended and retracted, and then selectively severed with cutter mechanism 484 after a sufficient length of bioabsorbable implant 360 is implanted. Similarly, in an embodiment, occluding device and delivery system comprise guide 480, cutter mechanism 484, and a bioabsorbable implant 460 having a customizable length.

In order to sever bioabsorbable implant 460, cutter mechanism 484 can comprise a blade 485 located on a distal end portion of implantation guide 380 and an actuatable component extending from the blade 485. Blade 485 can be oriented so that the cutting edge faces toward the center of implantation guide 480 lumen. Upon actuation, blade 485 moves across implantation guide 480 lumen, and can optionally reset itself. Blade 485 can comprise any material of suitable hardness to cut bioabsorbable implant 460. Blade 485 can be a hard polymer or a metallic component. Blade 485 can comprise a shape memory material, such as nitinol.

In accordance with another embodiment, a method of delivery comprise the steps of extending and/or retracting occluding device 400 through lumen of implantation guide 480; selectively severing occluding device 400 by actuatable cutter mechanism 484.

Figures 3, 3C, 4, 5:
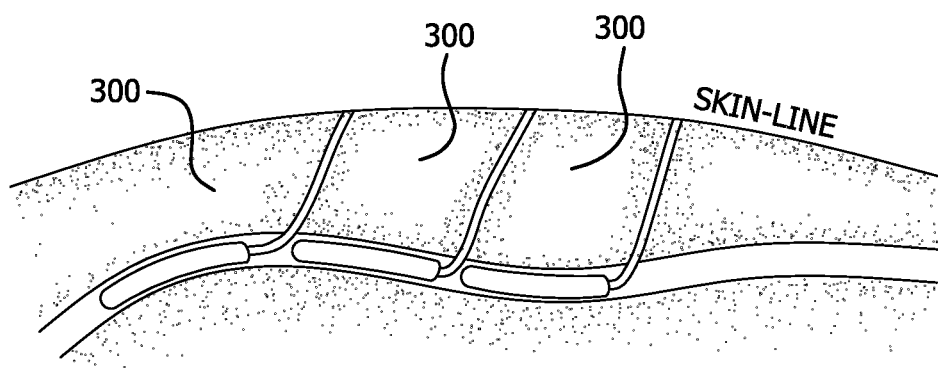
Figures 1, 5A:
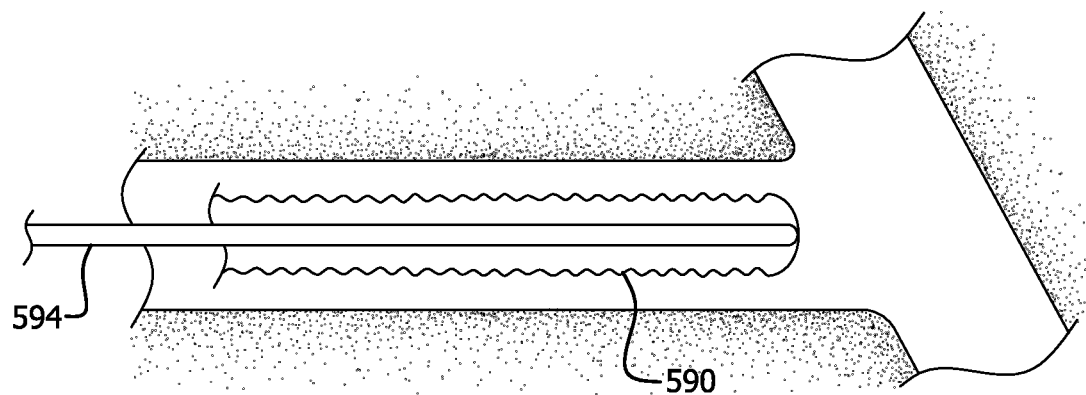
Figures 2, 5A:
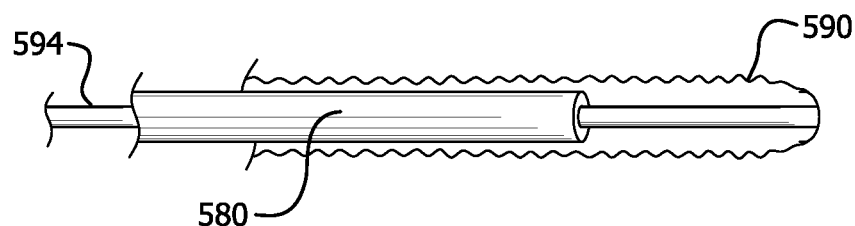
Figures 3, 5A:
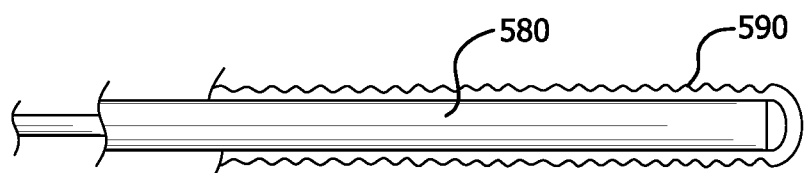
Figures 4, 5A:
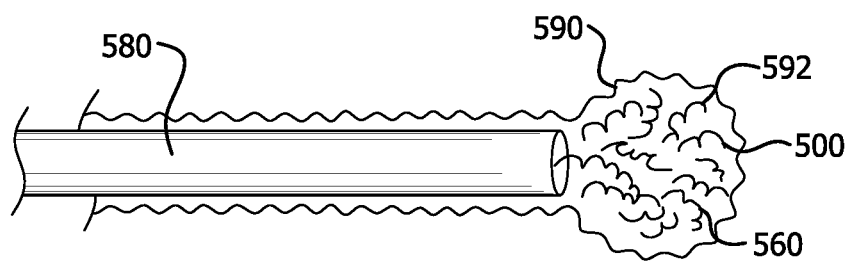
Figures 5, 5A:
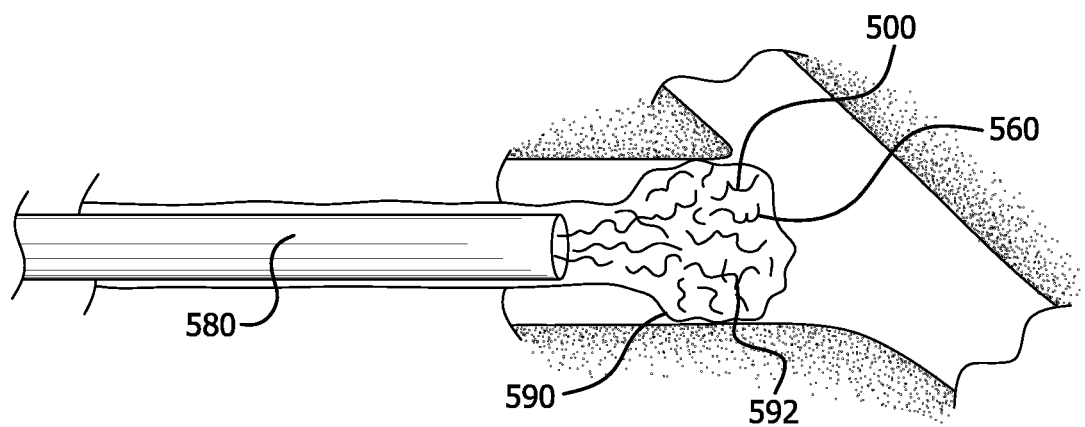

In an embodiment, with reference to FIG. 5A-1 to 5A-5, occluding device 500 can comprise a two-component bioabsorbable, lumen-occluding implant 560 wherein a first component comprises an occlusive member 590 defining a lumen or a cavity and a second component comprises an occlusive material 592. A further embodiment can also comprise a guidewire 594 and implantation guide 580 wherein occlusive member 590 is mounted around the distal end of guidewire 594. Implantation guide 580 can be configured to slide over guidewire 594 into the lumen or cavity of occlusive member 510, and after the retraction of guidewire 594, guide 580 can inject occlusive material 592 therein. For example, occlusive member 590 can be a sleeve closed at a distal end and dimensioned, in its unexpanded state, to be situated around or circumscribe the distal end of implantation guide 580.

In an embodiment, as occlusive material 592 is injected into the lumen, occlusive member 510 can distend or expand to occupy and approximately conform to the lumen of a vessel or other surrounding empty space. For example, occlusive member 590 can have a pleated or knitted conformation which can expand upon introduction of occlusive material 592. In other embodiments, occlusive member 590 can comprise a flexible material which stretches and/or expands upon introduction of occlusive material 592.

In other embodiments, occlusive member 590 can comprise an elongated, compliant, and convoluted conformation, which permits occlusive member 590 to be substantially straight when fitted or mounted around implantation guide 580 or guide wire 594, but as it 590 is released from implantation guide 580, it 590 takes on a convoluted conformation, which has a space-filling, occlusive effect.

In the same or different embodiments, occlusive member 590 is not distensible, but rather, bioabsorbable implant 500 facilitates the surrounding tissue conforming to the dimensions of the filled occlusive member (590 and 592), such as through the use of therapeutic agents like spasmodic agents, pro-coagulants, and/or biocompatible glues/tissue adhesives imbibed or infused into occlusive material 592, as well as manual compression.

Similar to other bioabsorbable implants described herein, occlusive material 592 can be optionally imbibed with a therapeutic agent. Occlusive member 590 can comprise a sufficiently porous or permeable material to permit transfer of the therapeutic agent to its outer surface.

Occlusive material 592 can comprise any bioabsorbable material that is suitable for filling occlusive member 590. In an embodiment, occlusive material 592 can be an injectable material, i.e., suitable for transporting through the lumen of implantation guide 580. For example, occlusive material 592 can comprise flowable material like a liquid, small particle solid materials and/or materials having loft, which can include non-woven web materials, tufts of fibers, a plurality of small spherical particles, or an emulsion. In a preferred embodiment, occlusive material 592 can comprise the non-woven, bioabsorbable web material made with poly(glycolide), also known as PGA, and poly(trimethylene carbonate), also known as TMC, described in U.S. Pat. No. 7,659,219 by Biran et al., entitled "Highly porous self-cohered web materials having hemostatic properties," which is hereby incorporated by reference in its entirety.

Occlusive member 590 comprises a bioabsorbable material formed into any thin-walled structural component that defines a lumen or cavity and can be expanded to occupy and approximately conform to a lumen vessel or a body cavity. Occlusive member 590 can comprise a bioabsorbable film or fabric that does not permit passage of occlusive material 592. Occlusive member 590 can comprise a distensible and compliant film or fabric to facilitate approximately conforming to the surrounding space.

Occlusive member 590 can be any shape suitable for occluding the desired lumen or body cavity. As mentioned above, occlusive member 590 can comprise an expandable sleeve. Expandable sleeve comprise a generally tubular shape having a proximal and a distal end and a lumen there through. The distal end can be permanently closed to contain occlusive material 592 as it is injected. Implantation guide 580 can be inserted through the proximal end to deliver occlusive material 592.

In order to close the occlusive member 590 so that occlusive material 592 does not leak from occlusive member 590 once implantation guide 580 is withdrawn, occlusive member 590 can be self-sealing or comprise a closure in order to at least substantially close the proximal end upon withdrawal of guide 580. Closure can comprise any mechanism or configuration that will close the proximal end of occlusive member 590. For example, closure can comprise self-collapsing section of occlusive member 590, such as an elastic band the will collapse down and close the proximal end of the occlusive member 590 upon retraction of implantation guide 580. Other closure embodiments can include a purse string, clip, or the like.

In an embodiment, wherein occlusive material 592 is injected along with a therapeutic agent, the transfer of the therapeutic agent may need to be restricted to permeating through only certain portions of occlusive member 590. According, occlusive member 590 can comprise sections or areas that remain impermeable to a therapeutic agent at least during the initial absorption phase. For example, having an impermeable end cap(s) on occlusive member 590 can mitigate undesired migration of a therapeutic agent. Areas of occlusive member 590 can be made impermeable by coating with a bioabsorbable sealant such as copolymers of lactic acid and glycolic acid (PLA/PGA), or varying the microstructure or thickness in these areas to make less permeable.

In accordance with another embodiment, a method of delivering occluding device 500 can comprise the steps of extending occlusive member 590 on guidewire 594 into a vessel; passing implantation guide 580 over guidewire 594 and into lumen of occlusive member 590; and injecting occlusive material 592 into lumen of occlusive member 590. Implantation guide 380 can be retracted as it injects occlusive material 592. Once implantation guide 580 is completely retracted, occlusive member 590 can collapse around the opening of occlusive member 590 through which the implantation guide 580 entered. Collapsing can be facilitated by a closure.

While bioabsorbable implants are discussed in relation to providing an occlusive effect, implants can be modified to cause a thrombolytic effect and can be inserted into a tissue or vasculature where a thrombolytic response is desired.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A vascular delivery device comprising:
an inner expandable member;
an outer drug delivery component comprising a drug infusible layer and being associated with the inner expandable member;
an elongate member comprising an expandable lumen configured to evert the inner expandable member; and
a hub comprising an infusion port and a ventilation port, wherein the infusion port is in fluid communication with the outer drug delivery component via an infusion lumen and the ventilation port is in fluid communication with the outer drug delivery component via a ventilation lumen.

2. The vascular delivery device of claim 1, wherein the outer drug delivery component is configured to deliver a therapeutic agent upon pressurizing the inner expandable member to a pressure threshold less than 20 psi above an ambient pressure.

3. The vascular delivery device of claim 2, wherein the therapeutic agent at least partially infuses the drug infusible layer before a portion of the therapeutic agent exits the ventilation lumen.

4. The vascular delivery device of claim 2, wherein the pressure threshold is less than 5 psi above the ambient pressure.

5. The vascular delivery device of claim 1, wherein the drug infusible layer comprises a wicking material.

6. The vascular delivery device of claim 1, wherein the drug infusible layer comprises an open pore, highly nodal membrane of PTFE.

7. The vascular delivery device of claim 1, wherein the drug infusible layer comprises an infusion path defined by at least one seam.

8. The vascular delivery device of claim 1, wherein the outer drug delivery component further comprises an outer barrier comprising a polymeric film, wherein the outer barrier is mounted around the drug infusible layer and configured to weep a therapeutic agent upon pressurizing the inner expandable member to a pressure threshold less than 20 psi above an ambient pressure.

9. The vascular delivery device of claim 1, wherein the inner expandable member comprises a substantially impermeable, tubular form and is not in fluid communication with the outer drug delivery component.

10. The vascular delivery device of claim 1, wherein the inner expandable member and the outer drug delivery component have a retracted position and an extended position.

11. The vascular delivery device of claim 1, wherein a proximal end of the inner expandable member is coupled to a distal portion of the elongate member.

12. The vascular delivery device of claim 1 further comprising a tethering device.

* * * * *